United States Patent
Ting et al.

(10) Patent No.: US 9,663,815 B2
(45) Date of Patent: *May 30, 2017

(54) CYTOSOLICALLY-ACTIVE PEROXIDASES AS REPORTERS FOR MICROSCOPY

(75) Inventors: Alice Y. Ting, Allston, MA (US); Jeffrey Daniel Martell, Somerville, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 384 days.

This patent is subject to a terminal disclaimer.

(21) Appl. No.: 14/345,309

(22) PCT Filed: Sep. 14, 2012

(86) PCT No.: PCT/US2012/055476
§ 371 (c)(1),
(2), (4) Date: Oct. 20, 2014

(87) PCT Pub. No.: WO2013/040388
PCT Pub. Date: Mar. 21, 2013

(65) Prior Publication Data
US 2015/0037829 A1 Feb. 5, 2015

Related U.S. Application Data

(60) Provisional application No. 61/535,839, filed on Sep. 16, 2011.

(51) Int. Cl.
*C12Q 1/28* (2006.01)
*G01N 23/04* (2006.01)

(52) U.S. Cl.
CPC ............... *C12Q 1/28* (2013.01); *G01N 23/04* (2013.01); *C12Y 111/01011* (2013.01)

(58) Field of Classification Search
CPC ... C12Q 1/28; C12Y 111/01011; G01N 23/04; G01N 33/581; G01N 2570/00; G01N 33/5023; G01N 33/6803; A01K 2217/05; A01K 2217/075; A01K 2227/105; A01K 2267/03; A01K 67/0276; A61K 38/00; A61K 48/00; A61K 39/00; C07K 14/47; C07K 2319/02; C07K 14/4711; C07K 14/195; C07K 14/21; C07K 14/22; C07K 14/485; C12N 9/0065
See application file for complete search history.

(56) References Cited

U.S. PATENT DOCUMENTS 9,012,170 B2 * 4/2015 Ting .................... G01N 33/581
435/28

FOREIGN PATENT DOCUMENTS

WO WO 2009/009142 A2 1/2009

OTHER PUBLICATIONS

GENBANK Submission; NCBI, Accession No. 4CCP_A; Finzel et al; Oct. 1, 2007.
GENBANK Submission; NCBI, Accession No. AAA61779; Chatfield et al.; Jun. 12, 1993.
GENBANK Submission; NCBI, Accession No. 2WD4_A; Raven et al.; Apr. 8, 2009.
Celik et al., Engineering the active site of ascorbate peroxidase. Eur J Biochem. Jan. 2001;268(1):78-85.
Goodin et al., Amino acid substitutions at tryptophan-51 of cytochrome c peroxidase: effects on coordination, species preference for cytochrome c, and electron transfer. Biochemistry. May 21, 1991;30(20):4953-62.
Leesch et al., Cytochrome c peroxidase-cytochrome c complex: locating the second binding domain on cytochrome c peroxidase with site-directed mutagenesis. Biochemistry. Aug. 22, 2000;39(33):10132-9.
Li et al., Membrane targeted horseradish peroxidase as a marker for correlative fluorescence and electron microscopy studies. Front Neural Circuits. Feb. 26, 2010;4:6. doi: 10.3389/neuro.04.006. 2010. eCollection 2010.
Mandelman et al., The role of quaternary interactions on the stability and activity of ascorbate peroxidase. Protein Sci. Oct. 1998;7(10):2089-98.
Pearl et al., Effect of single-site charge-reversal mutations on the catalytic properties of yeast cytochrome c peroxidase: evidence for a single, catalytically active, cytochrome c binding domain. Biochemistry. Mar. 4, 2008;47(9):2766-75. doi: 10.1021/bi702271r. Epub Jan. 31, 2008.
Seligman et al., Nondroplet ultrastructural demonstration of cytochrome oxidase activity with a polymerizing osmiophilic reagent, diaminobenzidine (DAB). J Cell Biol. Jul. 1968;38(1):1-14.
Shu et al., A genetically encoded tag for correlated light and electron microscopy of intact cells, tissues, and organisms. PLoS Biol. Apr. 2011;9(4):e1001041. doi: 10.1371/journal.pbio.1001041. Epub Apr. 5, 2011.
Baskin et al., Electron microscopic immunoperoxidase staining of insulin using 4-chloro-1-naphthol after osmium fixation. J Histochem Cytochem. Jul. 1982;30(7):710-2.
Baughman et al., Integrative genomics identifies MCU as an essential component of the mitochondrial calcium uniporter. Nature. Jun. 19, 2011;476(7360):341-5. doi: 10.1038/nature10234.
De Stefani et al., A forty-kilodalton protein of the inner membrane is the mitochondrial calcium uniporter. Nature. Jun. 19, 2011;476(7360):336-40. doi: 10.1038/nature10230.
Henriksen et al., The structures of the horseradish peroxidase C-ferulic acid complex and the ternary complex with cyanide suggest how peroxidases oxidize small phenolic substrates. J Biol Chem. Dec. 3, 1999;274(49):35005-11.
Koshiba, Cytosolic Ascorbate Peroxidase in Seedlings and Leaves of Maize (*Zea mays*). Plant Cell Physiol. 1993;34(5):713-721.

(Continued)

*Primary Examiner* — Debbie K Ware
(74) *Attorney, Agent, or Firm* — Wolf, Greenfield & Sacks, P.C.

(57) ABSTRACT

An imaging method comprising expressing in cells a Class I heme peroxidase, which optionally is fused with a protein of interest or a cellular localization signal peptide, and contacting the cells with a substrate of the Class I heme peroxidase to allow conversion of the substrate into a product via an oxidation reaction catalyzed by the Class I heme peroxidase, wherein the product releases a signal detectable by a microscope such as an electron microscope. Also disclosed herein are monomeric mutants of a Class I heme peroxidase and mutants of the enzyme that exhibit elevated enzymatic activity as compared to the corresponding wild-type counterpart.

18 Claims, 18 Drawing Sheets

(56) References Cited

OTHER PUBLICATIONS

Kumar et al. Synthesis and assembly of human beta 1 gap junctions in BHK cells by DNA transfection with the human beta 1 cDNA. J Cell Sci. Dec. 1995;108 ( Pt 12):3725-34.

Martell et al., Engineered ascorbate peroxidase as a genetically encoded reporter for electron microscopy. Nat Biotechnol. Nov. 2012;30(11):1143-8. doi: 10.1038/nbt.2375. Epub Oct. 21, 2012.

McKinney et al., A bright and photostable photoconvertible fluorescent protein. Nat Methods. Feb. 2009;6(2):131-3. doi: 10.1038/nmeth.1296. Epub Jan. 25, 2009.

Patterson et al., Characterization and crystallization of recombinant pea cytosolic ascorbate peroxidase. J Biol Chem. Jun. 24, 1994;269(25):17020-4.

Perocchi et al., MICU1 encodes a mitochondrial EF hand protein required for Ca(2+) uptake. Nature. Sep. 16, 2010;467(7313):291-6. doi: 10.1038/nature09358. Epub Aug. 8, 2010.

Ryan et al., Horseradish and soybean peroxidases: comparable tools for alternative niches? Trends Biotechnol. Aug. 2006;24(8):355-63. Epub Jul. 11, 2006.

Snapp et al., Formation of stacked ER cisternae by low affinity protein interactions. J Cell Biol. Oct. 27, 2003;163(2):257-69.

Sosinsky et al., Markers for correlated light and electron microscopy. Methods Cell Biol. 2007;79:575-91.

Uttamapinant et al., A fluorophore ligase for site-specific protein labeling inside living cells. Proc Natl Acad Sci U S A. Jun. 15, 2010;107(24):10914-9. doi: 10.1073/pnas.0914067107.Epub Jun. 7, 2010.

Lam et al., Directed evolution of APEX2 for electron microscopy and proximity labeling. Nat Methods. Jan. 2015;12(1):51-4. doi: 10.1038/nmeth.3179. Epub Nov. 24, 2014.

\* cited by examiner (a)

| APX Mutant (10 µM) | App. MW (kDa) | % High MW Aggr. |
|---|---|---|
| wt pAPX | 56 | 0 |
| K31S | 56 | 0 |
| A233D | 58 | 0 |
| I185K | 42 | 1 |
| K14D | 39 | 1 |
| A28K | 37 | 15 |
| E112K | 36 | 1 |
| E228K | 34 | 2 |
| D229K | 34 | 3 |
| A28K, E112K | 34 | 11 |
| K14D, D229K | 34 | 4 |
| K14D, E228K | 33 | 6 |
| E112K, E228K | 33 | 6 |
| K14D, E112K (mAPX) | 33 | 4 |
| E112K, D229K | 32 | 6 |
| A28K, E112K, D229K | 33 | 25 |
| K14D, E112K, D229K | 33 | 8 |
| K14D, E112K, E228K | 33 | 4 |
| A28K, E112K, E228K | 32 | 9 |

| Enzyme | $k_{cat}$ (s$^{-1}$) | $K_M$ (mM) | $k_{cat}/K_M$ (M$^{-1}$s$^{-1}$) | $k_{cat}/K_M$ rel. to wt |
|---|---|---|---|---|
| wt APX | 41 ± 5 | 13.0 ± 0.8 | 3.2 × 10$^3$ | 1.0 |
| HRP | 370 ± 30 | 2.7 ± 0.7 | 1.4 × 10$^5$ | 43.3 |
| W41F | 109 ± 8 | 4.2 ± 0.9 | 2.6 × 10$^4$ | 8.2 |
| G69F | 102 ± 2 | 23.2 ± 0.3 | 4.4 × 10$^3$ | 1.4 |
| FFA* | 44 ± 6 | 3.1 ± 0.8 | 1.4 × 10$^4$ | 4.5 |
| W41F + FFA* | 65 ± 2 | 1.2 ± 0.2 | 5.4 × 10$^4$ | 17.1 |
| G69F + FFA* | 97 ± 8 | 7.6 ± 0.7 | 1.3 × 10$^4$ | 4.0 |
| W41F + G69F | 100 ± 10 | 2.6 ± 0.3 | 3.9 × 10$^4$ | 12.1 |
| W41F + G69F + FFA* | 106 ± 6 | 1.2 ± 0.1 | 8.8 × 10$^4$ | 27.9 |
| K14D, E112K (mAPX) | 60 ± 10 | 13 ± 1 | 4.6 × 10$^3$ | 1.5 |
| K14D, E112K + W41F + FFA* | 79 ± 8 | 1.5 ± 0.5 | 5.3 × 10$^4$ | 16.6 |
| K14D, E112K + W41F (APEX) | 111 ± 1 | 4.3 ± 0.2 | 2.6 × 10$^4$ | 8.1 |

*FFA = D133A/T135F/K136F (c)

(a)

(b)

(a)

(b)

SEQUENCE LISTING

```
<160> NUMBER OF SEQ ID NOS: 22

<210> SEQ ID NO 1
<211> LENGTH: 250
<212> TYPE: PRT
<213> ORGANISM: Pisum sativum

<400> SEQUENCE: 1

Met Gly Lys Ser Tyr Pro Thr Val Ser Pro Asp Tyr Gln Lys Ala Ile
1               5                   10                  15

Glu Lys Ala Lys Arg Lys Leu Arg Gly Phe Ile Ala Glu Lys Lys Cys
            20                  25                  30

Ala Pro Leu Ile Leu Arg Leu Ala Trp His Ser Ala Gly Thr Phe Asp
        35                  40                  45

Ser Lys Thr Lys Thr Gly Gly Pro Phe Gly Thr Ile Lys His Gln Ala
    50                  55                  60

Glu Leu Ala His Gly Ala Asn Asn Gly Leu Asp Ile Ala Val Arg Leu
65                  70                  75                  80

Leu Glu Pro Ile Lys Glu Gln Phe Pro Ile Val Ser Tyr Ala Asp Phe
                85                  90                  95

Tyr Gln Leu Ala Gly Val Val Ala Val Glu Ile Thr Gly Gly Pro Glu
            100                 105                 110

Val Pro Phe His Pro Gly Arg Glu Asp Lys Pro Glu Pro Pro Pro Glu
        115                 120                 125

Gly Arg Leu Pro Asp Ala Thr Lys Gly Ser Asp His Leu Arg Asp Val
    130                 135                 140

Phe Gly Lys Ala Met Gly Leu Ser Asp Gln Asp Ile Val Ala Leu Ser
145                 150                 155                 160

Gly Gly His Thr Ile Gly Ala Ala His Lys Glu Arg Ser Gly Phe Glu
```

```
                165                 170                 175
Gly Pro Trp Thr Ser Asn Pro Leu Ile Phe Asp Asn Ser Tyr Phe Thr
            180                 185                 190
Glu Leu Leu Thr Gly Glu Lys Asp Gly Leu Leu Gln Leu Pro Ser Asp
                195                 200                 205
Lys Ala Leu Leu Thr Asp Ser Val Phe Arg Pro Leu Val Glu Lys Tyr
            210                 215                 220
Ala Ala Asp Glu Asp Val Phe Phe Ala Asp Tyr Ala Glu Ala His Leu
225                 230                 235                 240
Lys Leu Ser Glu Leu Gly Phe Ala Glu Ala
                245                 250

<210> SEQ ID NO 2
<211> LENGTH: 294
<212> TYPE: PRT
<213> ORGANISM: Saccharomyces cerevisiae

<400> SEQUENCE: 2

Thr Thr Pro Leu Val His Val Ala Ser Val Glu Lys Gly Arg Ser Tyr
1               5                   10                  15
Glu Asp Phe Gln Lys Val Tyr Asn Ala Ile Ala Leu Lys Leu Arg Glu
            20                  25                  30
Asp Asp Glu Tyr Asp Asn Tyr Ile Gly Tyr Gly Pro Val Leu Val Arg
        35                  40                  45
Leu Ala Trp His Ile Ser Gly Thr Trp Asp Lys His Asp Asn Thr Gly
    50                  55                  60
Gly Ser Tyr Gly Gly Thr Tyr Arg Phe Lys Lys Glu Phe Asn Asp Pro
65                  70                  75                  80
Ser Asn Ala Gly Leu Gln Asn Gly Phe Lys Phe Leu Glu Pro Ile His
                85                  90                  95
Lys Glu Phe Pro Trp Ile Ser Ser Gly Asp Leu Phe Ser Leu Gly Gly
            100                 105                 110
Val Thr Ala Val Gln Glu Met Gln Gly Pro Lys Ile Pro Trp Arg Cys
        115                 120                 125
Gly Arg Val Asp Thr Pro Glu Asp Thr Pro Asp Asn Gly Arg Leu
    130                 135                 140
Pro Asp Ala Asp Lys Asp Ala Gly Tyr Val Arg Thr Phe Phe Gln Arg
145                 150                 155                 160
Leu Asn Met Asn Asp Arg Glu Val Val Ala Leu Met Gly Ala His Ala
                165                 170                 175
Leu Gly Lys Thr His Leu Lys Asn Ser Gly Tyr Glu Gly Pro Trp Gly
            180                 185                 190
Ala Ala Asn Asn Val Phe Thr Asn Glu Phe Tyr Leu Asn Leu Leu Asn
        195                 200                 205
Glu Asp Trp Lys Leu Glu Lys Asn Asp Ala Asn Asn Glu Gln Trp Asp
    210                 215                 220
Ser Lys Ser Gly Tyr Met Met Leu Pro Thr Asp Tyr Ser Leu Ile Gln
225                 230                 235                 240
Asp Pro Lys Tyr Leu Ser Ile Val Lys Glu Tyr Ala Asn Asp Gln Asp
                245                 250                 255
Lys Phe Phe Lys Asp Phe Ser Lys Ala Phe Glu Lys Leu Leu Glu Asn
            260                 265                 270
Gly Ile Thr Phe Pro Lys Asp Ala Pro Ser Pro Phe Ile Phe Lys Thr
        275                 280                 285
```

```
Leu Glu Glu Gln Gly Leu
    290

<210> SEQ ID NO 3
<211> LENGTH: 740
<212> TYPE: PRT
<213> ORGANISM: Mycobacterium tuberculosis

<400> SEQUENCE: 3

Met Pro Glu Gln His Pro Pro Ile Thr Glu Thr Thr Gly Ala Ala
1               5                   10                  15

Ser Asn Gly Cys Pro Val Val Gly His Met Lys Tyr Pro Val Glu Gly
                20                  25                  30

Gly Gly Asn Gln Asp Trp Trp Pro Asn Arg Leu Asn Leu Lys Val Leu
            35                  40                  45

His Gln Asn Pro Ala Val Ala Asp Pro Met Gly Ala Ala Phe Asp Tyr
    50                  55                  60

Ala Ala Glu Val Ala Thr Ile Asp Val Asp Ala Leu Thr Arg Asp Ile
65                  70                  75                  80

Glu Glu Val Met Thr Thr Ser Gln Pro Trp Trp Pro Ala Asp Cys Gly
                85                  90                  95

His Tyr Gly Pro Leu Phe Ile Arg Met Ala Trp His Ala Ala Gly Thr
            100                 105                 110

Tyr Arg Ile His Asp Gly Arg Gly Gly Ala Gly Gly Met Gln Arg
            115                 120                 125

Phe Ala Pro Leu Asn Ser Trp Pro Asp Asn Ala Ser Leu Asp Lys Ala
            130                 135                 140

Arg Arg Leu Leu Trp Pro Val Lys Lys Lys Tyr Gly Lys Lys Leu Ser
145                 150                 155                 160

Trp Ala Asp Leu Ile Val Phe Ala Gly Asn Cys Ala Leu Glu Ser Met
                165                 170                 175

Gly Phe Lys Thr Phe Gly Phe Gly Phe Gly Arg Val Asp Gln Trp Glu
            180                 185                 190

Pro Asp Glu Val Tyr Trp Gly Lys Glu Ala Thr Trp Leu Gly Asp Glu
        195                 200                 205

Arg Tyr Ser Gly Lys Arg Asp Leu Glu Asn Pro Leu Ala Ala Val Gln
    210                 215                 220

Met Gly Leu Ile Tyr Val Asn Pro Glu Gly Pro Asn Gly Asn Pro Asp
225                 230                 235                 240

Pro Met Ala Ala Ala Val Asp Ile Arg Glu Thr Phe Arg Arg Met Ala
                245                 250                 255

Met Asn Asp Val Glu Thr Ala Ala Leu Ile Val Gly Gly His Thr Phe
            260                 265                 270

Gly Lys Thr His Gly Ala Gly Pro Ala Asp Leu Val Gly Pro Glu Pro
        275                 280                 285

Glu Ala Ala Pro Leu Glu Gln Met Gly Leu Gly Trp Lys Ser Ser Tyr
    290                 295                 300

Gly Thr Gly Thr Gly Lys Asp Ala Ile Thr Ser Gly Ile Glu Val Val
305                 310                 315                 320

Trp Thr Asn Thr Pro Thr Lys Trp Asp Asn Ser Phe Leu Glu Ile Leu
                325                 330                 335

Tyr Gly Tyr Glu Trp Glu Leu Thr Lys Ser Pro Ala Gly Ala Trp Gln
            340                 345                 350

Tyr Thr Ala Lys Asp Gly Ala Gly Ala Gly Thr Ile Pro Asp Pro Phe
        355                 360                 365
```

-continued

Gly Gly Pro Gly Arg Ser Pro Thr Met Leu Ala Thr Asp Leu Ser Leu
             370                 375                 380

Arg Val Asp Pro Ile Tyr Glu Arg Ile Thr Arg Arg Trp Leu Glu His
385                 390                 395                 400

Pro Glu Glu Leu Ala Asp Glu Phe Ala Lys Ala Trp Tyr Lys Leu Ile
                405                 410                 415

His Arg Asp Met Gly Pro Val Ala Arg Tyr Leu Gly Pro Leu Val Pro
            420                 425                 430

Lys Gln Thr Leu Leu Trp Gln Asp Pro Val Pro Ala Val Ser His Asp
        435                 440                 445

Leu Val Gly Glu Ala Glu Ile Ala Ser Leu Lys Ser Gln Ile Arg Ala
    450                 455                 460

Ser Gly Leu Thr Val Ser Gln Leu Val Ser Thr Ala Trp Ala Ala Ala
465                 470                 475                 480

Ser Ser Phe Arg Gly Ser Asp Lys Arg Gly Gly Ala Asn Gly Gly Arg
                485                 490                 495

Ile Arg Leu Gln Pro Gln Val Gly Trp Glu Val Asn Asp Pro Asp Gly
            500                 505                 510

Asp Leu Arg Lys Val Ile Arg Thr Leu Glu Glu Ile Gln Glu Ser Phe
        515                 520                 525

Asn Ser Ala Ala Pro Gly Asn Ile Lys Val Ser Phe Ala Asp Leu Val
530                 535                 540

Val Leu Gly Gly Cys Ala Ala Ile Glu Lys Ala Ala Lys Ala Ala Gly
545                 550                 555                 560

His Asn Ile Thr Val Pro Phe Thr Pro Gly Arg Thr Asp Ala Ser Gln
                565                 570                 575

Glu Gln Thr Asp Val Glu Ser Phe Ala Val Leu Glu Pro Lys Ala Asp
            580                 585                 590

Gly Phe Arg Asn Tyr Leu Gly Lys Gly Asn Pro Leu Pro Ala Glu Tyr
        595                 600                 605

Met Leu Leu Asp Lys Ala Asn Leu Leu Thr Leu Ser Ala Pro Glu Met
    610                 615                 620

Thr Val Leu Val Gly Gly Leu Arg Val Leu Gly Ala Asn Tyr Lys Arg
625                 630                 635                 640

Leu Pro Leu Gly Val Phe Thr Glu Ala Ser Glu Ser Leu Thr Asn Asp
                645                 650                 655

Phe Phe Val Asn Leu Leu Asp Met Gly Ile Thr Trp Glu Pro Ser Pro
            660                 665                 670

Ala Asp Asp Gly Thr Tyr Gln Gly Lys Asp Gly Ser Gly Lys Val Lys
        675                 680                 685

Trp Thr Gly Ser Arg Val Asp Leu Val Phe Gly Ser Asn Ser Glu Leu
    690                 695                 700

Arg Ala Leu Val Glu Val Tyr Gly Ala Asp Asp Ala Gln Pro Lys Phe
705                 710                 715                 720

Val Gln Asp Phe Val Ala Ala Trp Asp Lys Val Met Asn Leu Asp Arg
                725                 730                 735

Phe Asp Val Arg
            740

<210> SEQ ID NO 4
<211> LENGTH: 26
<212> TYPE: PRT
<213> ORGANISM: Artificial Sequence
<220> FEATURE:

```
<223> OTHER INFORMATION: ER localization sequence

<400> SEQUENCE: 4

Asp Pro Val Val Val Leu Gly Leu Cys Leu Ser Cys Leu Leu Leu Leu
1               5                   10                  15
Ser Leu Trp Lys Gln Ser Tyr Gly Gly Gly
            20                  25

<210> SEQ ID NO 5
<211> LENGTH: 24
<212> TYPE: PRT
<213> ORGANISM: Artificial Sequence
<220> FEATURE:
<223> OTHER INFORMATION: mitochondrial localization sequence

<400> SEQUENCE: 5

Met Leu Ala Thr Arg Val Phe Ser Leu Val Gly Lys Arg Ala Ile Ser
1               5                   10                  15
Thr Ser Val Cys Val Arg Ala His
            20

<210> SEQ ID NO 6
<211> LENGTH: 12
<212> TYPE: PRT
<213> ORGANISM: Artificial Sequence
<220> FEATURE:
<223> OTHER INFORMATION: nuclear export sequence

<400> SEQUENCE: 6

Leu Gln Leu Pro Pro Leu Glu Arg Leu Thr Leu Asp
1               5                   10

<210> SEQ ID NO 7
<211> LENGTH: 4
<212> TYPE: PRT
<213> ORGANISM: Artificial Sequence
<220> FEATURE:
<223> OTHER INFORMATION: ER localization sequence

<400> SEQUENCE: 7

Lys Asp Glu Leu
1

<210> SEQ ID NO 8
<211> LENGTH: 8
<212> TYPE: PRT
<213> ORGANISM: Artificial Sequence
<220> FEATURE:
<223> OTHER INFORMATION: FLAG tag

<400> SEQUENCE: 8

Asp Tyr Lys Asp Asp Asp Asp Lys
1               5

<210> SEQ ID NO 9
<211> LENGTH: 23
<212> TYPE: PRT
<213> ORGANISM: Artificial Sequence
<220> FEATURE:
<223> OTHER INFORMATION: Nuclear localization signal

<400> SEQUENCE: 9

Pro Lys Lys Lys Arg Lys Val Asp Pro Lys Lys Lys Arg Lys Val Asp
1               5                   10                  15
Pro Lys Lys Lys Arg Lys Val
```

```
<210> SEQ ID NO 10
<211> LENGTH: 10
<212> TYPE: PRT
<213> ORGANISM: Artificial Sequence
<220> FEATURE:
<223> OTHER INFORMATION: c-myc tag

<400> SEQUENCE: 10

Glu Gln Lys Leu Ile Ser Glu Glu Asp Leu
1               5                   10

<210> SEQ ID NO 11
<211> LENGTH: 14
<212> TYPE: PRT
<213> ORGANISM: Artificial Sequence
<220> FEATURE:
<223> OTHER INFORMATION: V5 tag

<400> SEQUENCE: 11

Gly Lys Pro Ile Pro Asn Pro Leu Leu Gly Leu Asp Ser Thr
1               5                   10

<210> SEQ ID NO 12
<211> LENGTH: 7
<212> TYPE: PRT
<213> ORGANISM: Artificial Sequence
<220> FEATURE:
<223> OTHER INFORMATION: linker sequence

<400> SEQUENCE: 12

Gly Ser Gly Gly Gly Gly Ser
1               5

<210> SEQ ID NO 13
<211> LENGTH: 12
<212> TYPE: PRT
<213> ORGANISM: Artificial Sequence
<220> FEATURE:
<223> OTHER INFORMATION: linker sequence

<400> SEQUENCE: 13

Lys Gly Ser Gly Ser Thr Ser Gly Ser Gly Thr Gly
1               5                   10

<210> SEQ ID NO 14
<211> LENGTH: 4
<212> TYPE: PRT
<213> ORGANISM: Artificial Sequence
<220> FEATURE:
<223> OTHER INFORMATION: solubilization sequence

<400> SEQUENCE: 14

Asn Ala Asn Pro
1

<210> SEQ ID NO 15
<211> LENGTH: 21
<212> TYPE: PRT
<213> ORGANISM: Artificial Sequence
<220> FEATURE:
<223> OTHER INFORMATION: Ig k-chain ss

<400> SEQUENCE: 15

Met Glu Thr Asp Thr Leu Leu Leu Trp Val Leu Leu Leu Trp Val Pro
1               5                   10                  15
```

Gly Ser Thr Gly Asp
            20

<210> SEQ ID NO 16
<211> LENGTH: 10
<212> TYPE: PRT
<213> ORGANISM: Artificial Sequence
<220> FEATURE:
<223> OTHER INFORMATION: linker

<400> SEQUENCE: 16

Lys Gly Ser Gly Ser Thr Ser Gly Ser Gly
1               5                   10

<210> SEQ ID NO 17
<211> LENGTH: 4
<212> TYPE: PRT
<213> ORGANISM: Artificial Sequence
<220> FEATURE:
<223> OTHER INFORMATION: linker

<400> SEQUENCE: 17

Pro Val Ala Thr
1

<210> SEQ ID NO 18
<211> LENGTH: 10
<212> TYPE: PRT
<213> ORGANISM: Artificial Sequence
<220> FEATURE:
<223> OTHER INFORMATION: linker

<400> SEQUENCE: 18

Ser Gly Leu Arg Ser Gly Gly Ser Gly Gly
1               5                   10

<210> SEQ ID NO 19
<211> LENGTH: 17
<212> TYPE: PRT
<213> ORGANISM: Artificial Sequence
<220> FEATURE:
<223> OTHER INFORMATION: linker

<400> SEQUENCE: 19

Cys Pro Thr Phe Leu Tyr Lys Val Val Asp Leu Glu Gly Pro Arg Phe
1               5                   10                  15

Glu

<210> SEQ ID NO 20
<211> LENGTH: 10
<212> TYPE: PRT
<213> ORGANISM: Artificial Sequence
<220> FEATURE:
<223> OTHER INFORMATION: linker

<400> SEQUENCE: 20

Gly Gly Ser Gly Gly Ser Gly Gly Ser Arg
1               5                   10

<210> SEQ ID NO 21
<211> LENGTH: 68
<212> TYPE: PRT
<213> ORGANISM: Artificial Sequence
<220> FEATURE:
<223> OTHER INFORMATION: IMS localization sequence

```
<400> SEQUENCE: 21

Met Tyr Arg Leu Leu Ser Ser Val Thr Ala Arg Ala Ala Ala Thr Ala
1               5                   10                  15

Gly Pro Ala Trp Asp Gly Gly Arg Arg Gly Ala His Arg Arg Pro Gly
            20                  25                  30

Leu Pro Val Leu Gly Leu Gly Trp Ala Gly Gly Leu Gly Leu Gly Leu
        35                  40                  45

Gly Leu Ala Leu Gly Ala Lys Leu Val Val Gly Leu Arg Gly Ala Val
    50                  55                  60

Pro Ile Gln Ser
65

<210> SEQ ID NO 22
<211> LENGTH: 250
<212> TYPE: PRT
<213> ORGANISM: Pisum sativum

<400> SEQUENCE: 22

Arg Gly Lys Ser Tyr Pro Thr Val Ser Pro Asp Tyr Gln Lys Ala Ile
1               5                   10                  15

Glu Lys Ala Lys Arg Lys Leu Arg Gly Phe Ile Ala Glu Lys Lys Cys
            20                  25                  30

Ala Pro Leu Ile Leu Arg Leu Ala Trp His Ser Ala Gly Thr Phe Asp
        35                  40                  45

Ser Lys Thr Lys Thr Gly Gly Pro Phe Gly Thr Ile Lys His Gln Ala
    50                  55                  60

Glu Leu Ala His Gly Ala Asn Asn Gly Leu Asp Ile Ala Val Arg Leu
65                  70                  75                  80

Leu Glu Pro Ile Lys Glu Gln Phe Pro Ile Val Ser Tyr Ala Asp Phe
                85                  90                  95

Tyr Gln Leu Ala Gly Val Val Ala Val Glu Ile Thr Gly Gly Pro Glu
            100                 105                 110

Val Pro Phe His Pro Gly Arg Glu Asp Lys Pro Glu Pro Pro Pro Glu
        115                 120                 125

Gly Arg Leu Pro Asp Ala Thr Lys Gly Ser Asp His Leu Arg Asp Val
    130                 135                 140

Phe Gly Lys Ala Met Gly Leu Ser Asp Gln Asp Ile Val Ala Leu Ser
145                 150                 155                 160

Gly Gly His Thr Ile Gly Ala Ala His Lys Glu Arg Ser Gly Phe Glu
                165                 170                 175

Gly Pro Trp Thr Ser Asn Pro Leu Ile Phe Asp Asn Ser Tyr Phe Thr
            180                 185                 190

Glu Leu Leu Thr Gly Glu Lys Asp Gly Leu Leu Gln Leu Pro Ser Asp
        195                 200                 205

Lys Ala Leu Leu Thr Asp Ser Val Phe Arg Pro Leu Val Glu Lys Tyr
    210                 215                 220

Ala Ala Asp Glu Asp Val Phe Phe Ala Asp Tyr Ala Glu Ala His Leu
225                 230                 235                 240

Lys Leu Ser Glu Leu Gly Phe Ala Glu Ala
                245                 250
```

CYTOSOLICALLY-ACTIVE PEROXIDASES AS REPORTERS FOR MICROSCOPY

RELATED APPLICATIONS

This application is a national stage filing under U.S.C. §371 of PCT International Application PCT/US2012/055476, filed Sep. 14, 2012, which claims the benefit under 35 U.S.C. §119(e) of U.S. Provisional Application Ser. No. 61/535,839, entitled "Cytosolically-Active Peroxidase as Reporters for Microscopy," filed on Sep. 16, 2011, which are herein incorporated by reference in their entirety.

GOVERNMENT SUPPORT

This invention was made with Government support under Grant No. OD003961 awarded by the National Institutes of Health. The Government has certain rights in the invention.

BACKGROUND OF THE INVENTION

Electron microscopy (EM) offers far better spatial resolution than fluorescence microscopy and therefore is a very important tool for cell biology. For example, mitochondria are just a few pixels wide by fluorescence but details and subcompartments can be seen by EM. However, a major limitation of EM is the lack of a fluorescent protein equivalent for highlighting specific proteins of interest.

Two existing genetically encoded reporters for EM are Horse Radish Peroxidase (HRP) and mini-singlet oxygen generator (SOG), both generating contrast by catalyzing the polymerization of a diaminobenzidine (DAB) into an osmiophilic polymer. Photo oxidation of miniSOG requires laser and blown oxygen. As such, use of miniSOG as an EM reporter is limited to small fields of view. HRP is a much easier to use, less temperamental, and more robust reporter than miniSOG, but it only works in the secretory pathway, such as in the endoplasmic reticulum (ER) and the Golgi apparatus, or on cell surfaces. It is inactive in any other cellular compartment, e.g., cytosol, due to disruption of the four disulfide bonds in this enzyme. Other reporters are prone to inactivation due to the strong fixation typically employed in EM.

It is of great importance to develop sensitive and robust reporters for use in EM.

SUMMARY OF THE INVENTION

The present disclosure is based on the unexpected discoveries that a number of ascorbate peroxidases (APX), including both wild-type APX and APX mutants (e.g., monomeric mutants and high activity mutants), successfully converted various enzyme substrates (e.g., DAB and Amplex Red) into signal-releasing products (e.g., osmiophilic polymers and fluorescent dyes) in specific subcellular compartments (e.g., cytosol and mitochondria), indicating that this family of enzymes are cytosolically active and therefore are useful in microscopy imaging, particularly in EM imaging. The present disclosure is also based on the development of a number of APX mutants that exist in monomer form and/or exhibit elevated enzymatic activity relative to their wild-type counterparts.

Accordingly, one aspect of the present disclosure relates to an imaging method, which comprises (i) providing a sample (e.g., a tissue sample) containing a cell that expresses a Class I heme peroxidase (e.g., a monomeric enzyme), or a fusion protein comprising (a) the Class I heme peroxidase and (b) a protein of interest or a cellular localization signal peptide, and (ii) contacting the sample with a substrate of the Class I heme peroxidase to allow conversion of the substrate into a product via an oxidation reaction catalyzed by the Class I heme peroxidase, wherein the product releases a signal detectable by a microscope (e.g., an electron microscope). In certain embodiments, the method further comprises detecting the signal under a microscope. The peroxidase substrates for use in the imaging methods described herein can be a phenol (e.g., guaiacol, pyrogallol, Amplex UltraRed, dihydrofluorescin, p-cresol, dopamine, 3-methylphenol, 4-methoxyphenol, 4-hydroxybenzaldehyde, 5-aminosalicylic acid, or 4-chloro-1-naphthol) or an aniline (e.g., diaminobenzidine (DAB), 3-amino-9-ethylcarbazole, o-phenylenediamine, 3,3',5,5'-tetramethylbenzidine, o-diansidine, 5-aminosalicylic acid, Luminol, 4-aminophthalhydrazide, N-(6-Aminohexyl)-N-ethylisoluminol, N-(4-Aminobutyl)-N-ethylisoluminol, 3-methylaniline, 4-methylaniline, or 4-methoxyaniline). Alternatively, the peroxidase substrate can be 3-methyl-2-benzothiazolinone hydrazine or 2,2'-azino-bis(3-ethylbenzthiazoline-6-sulfonic acid). When necessary, the expression of the Class I heme peroxidase or the fusion protein containing such can be under the control of a cell-type specific promoter.

In some examples, the imaging method described herein involves expression of a fusion protein that comprises the Class I heme peroxidase and a protein of interest, e.g., a mitochondrial protein, mitochondrial matrix protein, a mitochondrial intermembrane space protein, a mitochondrial inner membrane protein, a mitochondrial outer membrane protein (facing cytosol), a Golgi protein, an endoplasmic reticulum lumen protein, an endoplasmic reticulum membrane protein (facing cytosol), a cell surface protein, a secreted protein, a nuclear protein, a vesicle protein, a cell skeleton protein, a cell skeleton-binding protein, a motor protein, a gap junction protein, a chromatin-organizing protein, a transcription factor protein, a DNA polymerase protein, a ribosomal protein, a synaptic protein, or an adhesion protein. In other examples, the fusion protein comprises the Class I heme peroxidase and a cellular localization signal peptide, such as an ER-targeting signal peptide, a Golgi-targeting signal peptide, a mitochondria-targeting signal peptide, a nuclear localization signal peptide, or a nuclear export signal peptide. Examples of cellular localization signal peptides include, but are not limited to, DPVVVLGLCLSCLLLLSLWKQSYGGG (SEQ ID NO: 4), MLATRVFSLVGKRAISTSVCVRAH (SEQ ID NO:5), LQLPPLERLTLD (SEQ ID NO:6), and KDEL (SEQ ID NO:7). When necessary, either the Class I heme peroxidase or the fusion protein can comprise a protein tag.

In some examples, the cell that expresses the Class I heme peroxidase or the fusion protein can be a mammalian cell, a bacterial cell, or a yeast cell. Either live cells or fixed cells can be used in the imaging method described herein for detecting a signal released from the product of a Class I heme peroxidase.

The Class I heme perodixase used in the method described herein can be an ascorbate peroxidase (APX), a yeast cytochrome c peroxidase (CCP), or a bacterial catalase-peroxidase (BCP), which can either be a wild-type enzyme or a functional mutant thereof.

In some embodiments, the Class I heme peroxidase is a monomeric mutant of a wild-type Class I heme peroxidase. In one example, the monomeric mutant is a mutant of an APX, which, as compared to its wild-type counterpart, contains one or more mutations at positions corresponding to K14, E17, K18, K20, R21, R24, A28, E106, E112, I185, E228, and D229 in SEQ ID NO:1. Such a mutated APX can comprise one or more of amino acid substitutions corresponding to K14D, E17N, K20A, R21L, A28K, E112K, E228K, and D229K. In other examples, the mutated APX comprises substitutions corresponding to A28K/E112K, K14D/D229K, K14D/E228K, K14D/E112K, E112K/D229K, A28K/E112K/D229K, K14D/E112K/D229K, K14D/E112K/E228K, or A28K/E112K/E228K. Examples of the APX monomeric mutants include, but are not limited to, single mutant K14D, A28K, E112K, E228K, or D229K, double mutant A28K/E112K, K14D/E112K (mAPX), K14D/E228K, K14D/D229K, E112K/E228K, or E112K/D229K, triple mutant E17N/K20A/R21L, A28K/E112K/D229K, K14D/W41F/E112K, K14D/E112K/D229K, K14D/E112K/E228K, or A28K/E112K/E228K. Alternatively, the monomeric mutant is a mutated BCP comprising one or more mutations that disrupt dimer formation.

In other embodiments, the Class I heme peroxidase is a mutant of a wild-type Class I heme peroxidase (e.g., a wild-type APX), wherein the mutant has elevated enzymatic activity as compared to the wild-type peroxidase. Such a high activity APX mutant can comprise one or more amino acid substitutions at positions corresponding to W41, G69, D133, T135, and K136 in SEQ ID NO:1. In some examples, the mutant APX comprises one or more of amino acid substitutions corresponding to W41F, G69F, D133A, T135F, and K136F. Examples of high activity APX mutants include, but are not limited to, W41F, G69F, W41F/G69F, D133A/T135F/K136F, W41F/D133A/T135F/K136F, G69F/D133A/T135F/K136F, and W41F/G69F/D133A/T135F/K136F.

The high activity Class I heme peroxidase mutant can also be a mutated yeast CCP, which, as compared to its wild-type counterpart, comprises one or more amino acid substitutions at positions corresponding to W51, S81, D146, D148, K149, and G186 in SEQ ID NO:2. In some examples, the native amino acid residue(s) at one or more of positions corresponding to W51, S81, D148, K149, and G186 in SEQ ID NO:2 can be replaced with F. In another example, the mutated yeast CCP comprises an amino acid residue substitution at a position corresponding to D146 in SEQ ID NO:2, wherein the native D residue can be replaced with A.

Alternatively, the high activity Class I heme peroxidase mutant is a mutant of a BCP, which, as compared to its wild-type counterpart, comprises one or more amino acid residue substitutions at positions corresponding to W107, D137, N231, E223, and G316 in SEQ ID NO:3. In other examples, one or more of the native amino acid residues at positions corresponding to W107, D137, E223, and G316 in SEQ ID NO:3 can be replaced with F. In some examples, the mutated BCP comprises an amino acid residue substitution at a position corresponding to N231 in SEQ ID NO:3, wherein the native amino acid residue at that position can be replaced with A.

When desired, a Class I heme peroxidase mutant can be a monomeric enzyme exhibiting elevated enzymatic activity as relative to the corresponding wild-type counterpart, e.g., containing one or more mutations that disrupt dimer formation and one or more mutations that lead to elevated enzymatic activity, for example, those described herein. In some examples, such a mutant is an APX mutant that is a combination of: (a) single mutant K14D, single mutant E112K, single mutant E228K, single mutant D229K, double mutant K14D/E112K, double mutant K14D/E228K, double mutant K14D/D229K, triple mutant E17N/K20A/R21L, or triple mutant K14D/W41F/E112K; and (b) single mutant W41F, single mutant G69F, single mutant G174F, double mutant W41F/G69F, triple mutant D133A/T135F/K136F, quadruple mutant W41F/D133A/T135F/K136F, quadruple mutant G69F/D133A/T135F/K136F, or quintuple mutant W41F/G69F/D133A/T135F/K136F. Examples include, but are not limited to, K14D/E112K/W41F(APEX) and K14D/E112K/W41F/D133A/T135F/K136F.

Also within the scope of the present disclosure are any of the Class I heme peroxidase mutants described herein and its encoding nucleic acid (both in isolated form), as well as vectors (e.g., expression vectors in which the coding sequence is in operably linkage with a suitable promoter) comprising the encoding nucleic acids, and host cells (e.g., bacterial cells, yeast cells, or mammalian cells) comprising the vectors, e.g., expression vectors for producing the peroxidase mutant. The nucleic acid encoding any of the Class I heme peroxidase mutants as described above can be linked in frame with a second nucleotide sequence that encodes a protein of interest or a cellular localization signal peptide, e.g., those described above.

An "isolated polypeptide" or "isolated polynucleotide" as used herein refers to a polypeptide or polynucleotide that is substantially free from naturally associated molecules, i.e., the naturally associated molecules constituting at most 20% by dry weight of a preparation containing the polypeptide or polynucleotide. Purity can be measured by any appropriate method, e.g., column chromatography, polyacrylamide gel electrophoresis, and HPLC.

The present disclosure also provides a method of producing any of the Class I heme peroxidase mutants described herein. The method comprises culturing a host cell that comprises an expression vector for expressing a Class I heme peroxidase mutant as described herein, which can be fused in frame with a protein of interest or a cellular localization signal peptide, collecting cells thus obtained for isolation of the Class I heme peroxidase mutant, and optionally, isolating the Class I heme peroxidase mutant from the cultured cells or culture medium.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

DETAILED DESCRIPTION

Figure 1:
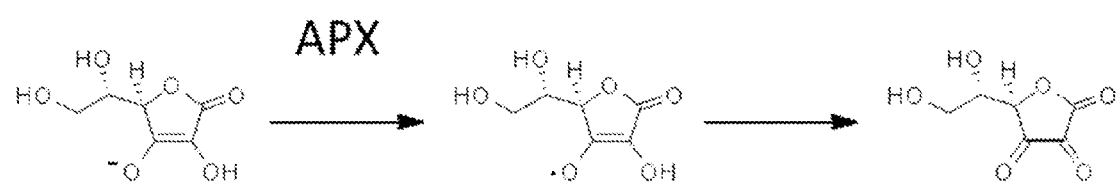
FIG. 1 is a diagram showing the reaction ascorbate perosidase (APX) catalyzes in nature.

It was discovered that, unexpectedly, both wild-type and mutated ascorbate peroxidase (APX) enzymes, a subfamily of Class I heme peroxidase, are enzymatically active in mammalian cells and remain active after the cells have been subjected to membrane-preserving fixation, resulting in the generation of minimally-diffusive reaction products that cannot cross membranes. Thus, Class I heme peroxidases, either wild-type or functional mutants, can be used as reporters in imaging methods for, e.g., determining protein topology within membranes.

Accordingly, described herein are imaging methods involving expression of a Class I heme peroxidase in cells and incubation of the cells with a suitable substrate under conditions allowing conversion of the substrate into a product that releases a signal detectable under a microscope. Also described herein are Class I heme peroxidase (e.g., APX) mutants that are in monomeric form and/or exhibit higher enzymatic activity as relative to the wild-type counterpart; nucleic acids encoding such enzyme mutants, vectors (e.g., expression vectors) and host cells comprising the nucleic acids, and methods for producing the mutants.

Class I Heme Peroxidases

Class I heme peroxidase (or heme peroxidase), as used herein, refers to a heme-containing peroxidases that use hydrogen peroxide as the electron acceptor to catalyze a number of oxidative reactions. In nature, Class I heme peroxidases are found in plants, fungi, and bacteria, and include at least three subfamilies: yeast cytochrome c peroxidase (CCP), ascorbate peroxidase (APX), and bacterial catalase-peroxidase (BCP). CCP is a soluble protein found in the mitochondrial electron transport chain in yeast, where it protects yeast cells against toxic peroxides. APX is the main enzyme responsible for hydrogen peroxide removal in chloroplasts and cytosol of higher plants. Dalton, 1991, *Ascorbate peroxidase*, 2:139-153. Naturally, this enzyme, around 28 kD in molecular weight, is expressed in plant cytosol. It contains no disulfides or $Ca^{+2}$ ions and forms dimers. BCP is a bacterial enzyme that exhibits both peroxidase and catalase activities. It is thought that catalase-peroxidase provides protection to cells under oxidative stress. Welinder, 1991, Biochim. Biophys. Acta 1080(3): 215-220.

Examples of wild-type Class I heme peroxidases are provided in Table 1 below:

TABLE 1

Exemplary Class I Heme Peroxidases

| Enzyme | Species | Genbank accession # or PDB (protein data bank) code |
|---|---|---|
| Ascorbate peroxidase | *Pisum sativum* (pea) | CAA43992.1 |
| Ascorbate peroxidase | *Glycine max* (soybean) | AAA61779.1 |

TABLE 1-continued

Exemplary Class I Heme Peroxidases

| Enzyme | Species | Genbank accession # or PDB (protein data bank) code |
|---|---|---|
| Cytochome c peroxidase | Saccharomyces cerevisiae (yeast) | PDB: 2CYP |
| Leishmania major peroxidase | Leishmania major (a parasitic protozoa) | PDB: 3RIV |
| Mycobacterium tuberculosis catalase-peroxidase | Mycobacterium tuberculosis | PDB: 1SJ2 |

Also provided below are amino acid sequences of representative Class I heme peroxidase in each of the three subfamilies:

```
Pea APX (SEQ ID NO: 1):
  1 mgksyptvsp dyqkaiekak rklrgfiaek kcaplilrla
    whsagtfdsk tktggpfgti 61 khgaelahga nngldiavrl lepikeqfpi vsyadfyqla
    gvvaveitgg pevpfhpgre 121 dkpepppegr lpdatkgsdh lrdvfgkamg lsdqdivals
    gghtigaahk ersgfegpwt 181 snplifdnsy ftelltgekd gllqlpsdka lltdsvfrpl
    vekyaadedv ffadyaeahl 241 klselgfaea S. cerevisiae CCP (SEQ ID NO: 2):
  1 ttplvhvasv ekgrsyedfq kvynaialkl reddeydnyi
    gygpvlvrla whisgtwdkh 61 dntggsyggt yrfkkefndp snaglqngfk flepihkefp
    wissgdlfsl ggvtavqemq 121 gpkipwrcgr vdtpedttpd ngrlpdadkd agyvrtffqr
    lnmndrevva lmgahalgkt 181 hlknsgyegp wgaannvftn efylnllned wklekndann
    eqwdsksgym mlptdysliq 241 dpkylsivke yandqdkfffk dfskafekll engitfpkda
    pspfifktle eqgl M. tuberculosis BCP (SEQ ID NO: 3):
  1 mpeqhppite tttgaasngc pvvghmkypv egggnqdwwp
    nrlnlkvlhq npavadpmga 61 afdyaaevat idvdaltrdi eevmttsqpw wpadcghygp
    lfirmawhaa gtyrihdgrg 121 gagggmqrfa pinswpdnas ldkarrllwp vkkkygkkls
    wadlivfagn calesmgfkt 181 fgfgfgrvdq wepdevywgk eatwlgdery sgkrdlenpl
    aavqmgliyv npegpngnpd 241 pmaaavdire tfrrmamndv etaalivggh tfgkthgagp
    adlvgpepea apleqmglgw 301 kssygtgtgk daitsgievv wtntptkwdn sfleilygye
    weltkspaga wqytakdgag 361 agtipdpfgg pgrsptmlat dlslrvdpiy eritrrwleh
    peeladefak awyklihrdm 421 gpvarylgpl vpkqtllwqd pvpavshdlv geaeiaslks
    qirasgltvs qlvstawaaa 481 ssfrgsdkrg ganggrirlq pqvgwevndp dgdlrkvirt
    leeiqesfns aapgnikvsf 541 adlvvlggca aiekaakaag hnitvpftpg rtdasqeqtd
    vesfavlepk adgfrnylgk 601 gnplpaeyml ldkanlltls apemtvlvgg lrvlganykr
    lplgvfteas esltndffvn 661 lldmgitwep spaddgtyqg kdgsgkvkwt gsrvdlvfgs
    nselralvev ygaddaqpkf 721 vqdfvaawdk vmnldrfdvr
```

Examples of other APX enzymes include, but are not limited to *Medicago truncatula* Cytosolic ascorbate peroxidase (e.g., GenBank accession no. XP_003606510), *Vigna unguiculata* cytosolic ascorbate peroxidase (e.g., GenBank accession no. AAB03844], *Glycine max* L-ascorbate peroxidase 2 (e.g., GenBank accession no. NP_001235587), *Ziziphus jujuba* ascorbate peroxidase (e.g., GenBank accession no. BAM28755), *Camellia sinensis* ascorbate peroxidase (GenBank accession no. ABD97259), and *Solanum lycopersicum* cytosolic ascorbate peroxidase (e.g., GenBank accession no. NP_001234788).

Examples of other CCP enzymes include, but are not limited to, *Saccharomyces cerevisiae* Ccp1p (e.g., GenBank accession no. EIWO9306), *Saccharomyces arboricola* ccp1p (e.g., GenBank accession no. EJS42830), and *Saccharomyces kudriavzevii* CCP1 (e.g., GenBank accession no. EJT43981). Examples of other BCP enzymes include, but are not limited to, *Mycobacterium tuberculosis* catalase-peroxidase (e.g., Genbank accession no. AAK06516 and AAA18230), *Streptomyces griseoaurantiacus* catalase/peroxidase (e.g., GenBank accession no. ZP_08290983), and *Rhodococcus opacus* catalase-peroxidase (e.g., GenBank accession no. YP_002782511).

Class I heme peroxidases in each subfamily are highly homologous across species. Thus, each subfamily of Class I heme peroxidases from other yeast, plant or bacterial species are well known in the art and can be retrieved from, e.g., GenBank or Protein Data Bank, using any of the above described enzymes as a query.

In addition to wild-type enzymes as those described above, the Class I heme peroxidases described herein also include functional mutants of native enzymes. A functional mutant may share at least 80% sequence identity (e.g., 85%, 90%, 95%, 97%, 98%, or 99%) with its wild-type counterpart and preserves the desired enzymatic activity. The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

Alternative or in addition, the enzyme mutants described herein may contain mutations (e.g., amino acid residue substitution) at up to 20 positions (e.g., up to 15, 10, or 5 positions) as relative to a wild-type counterpart.

It was known in the art that mutations introduced into non-functional domains of an enzyme are unlikely to affect the activity of that enzyme. Accordingly, the functional mutants of Class I heme peroxidases may contain mutations in non-functional domains of a wild-type enzyme. Crystal structures of a number of representative Class I heme peroxidases have been determined already. Bertrand et al., 2004, J. Biol. Chem. 279:38991-38999; Finzel et al., J. Biol. Chem. 1984, 259:13027-13036; and Jasion et al., 2011, J. Biol. Chem. 286:24608-24615. In addition, it was known in the art that this family of peroxidases is homologous across species. Thus, functional domains of this enzyme can be determined based on the known crystal structures and by comparing amino acid sequences across species. One example is provided below:

The structure-function correlation of pea APX (SEQ ID NO:1, GenBank accession no. CAA43992), a representative APX, was well known in the art. For example, positions 34, 35, 38, 132-134, 145, 159, 160, 162, 163, 165-169, 172, 173, 179, 205, 207, 235 and 239 are suggested as residues involved in heme binding; positions 111, 163, 165, 166, 168, 193, 202, and 203 are suggested as residues involved in substrate binding; and positions 164, 180, 182, 185, 187, and 189 are suggested as residues involved in ion binding. Given the cross-species sequence homology, the structure-function correlation of other APX enzymes can be readily determined based on such correlation of pea APX.

Alternatively, conservative amino acid substitutions may be introduced into a wild-type peroxidase to provide functionally equivalent mutants. As used herein, a "conservative amino acid substitution" refers to an amino acid substitution that does not alter the relative charge or size characteristics of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the peroxidase mutants described herein are monomeric mutants of APX or BCP. A monomeric mutant as described herein refers to a mutant of a wild-type dimeric Class I heme peroxidase (e.g., a naturally-occurring APX or CCP) that can exist in monomer form. Preferably, at least 50% (e.g., 60%, 70%, 80%, 90%, or 95%) of such a mutant is present in monomer form when expressed in host cells. Such mutants can be prepared by introducing mutations at amino acid residues that are involved in dimerization, which can be identified via sequence alignment with a native monomeric APX (e.g., a maize APX; see Koshiba et al., Plant and Cell Physiology 34: 713-721, 1993). In some examples, such a monomeric mutant share at least 80% (e.g., 85%, 90%, 95%, or 98%) sequence homology to a wild-type reference peroxidase (e.g., an APX or CCP).

Figure 4:
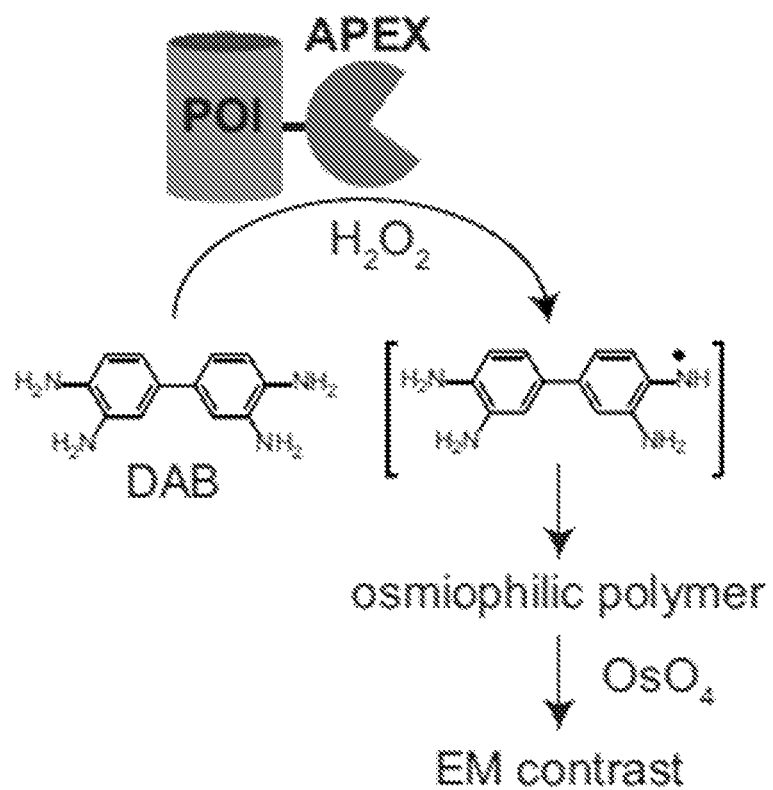
FIG. 4 is a diagram showing the electron microscopy reporting scheme and characterization of APX mutant APEX (enhanced APX, K14D/E112K/W41F. See also Examples 1 and 2 below) oligomerization state. (a) a schematic illustration showing use of a fusion protein containing the APEX reporter and a cellular protein of interest (POI) to convert DAB into osmiophilic polymers in the presence of $H_2O_2$ and subsequent generation of EM contrast in the presence of $OsO_4$. (b) a schematic illustration showing the 3-D structure of wild-type APX dimer and residues involved in formation of the dimer interface (shown at left; from PDB ID 1APX17). (c) a table listing the approximate molecular weights and percentages of high molecular-weight aggregates of wild-type (wt) and a number of mutated APX mutant, as analyzed by gel filtration chromatography. (d) Gel filtration analysis of mAPX, wt APX, and APEX at concentrations ranging from 250 nM to 250 µM. Dimerization of mAPX and APEX are not detected at <10 µM but some dimerization is seen at concentrations >50 µM. For comparison, similar analyses were performed under identical conditions for the fluorescent protein markers mEos2, EYFP, and mApple, as well as miniSOG 2. Error bars represent the standard deviation of 2-3 independent measurements. For data points which have standard deviation values smaller than the height of the marker, no error bars are shown.
Figure 4:
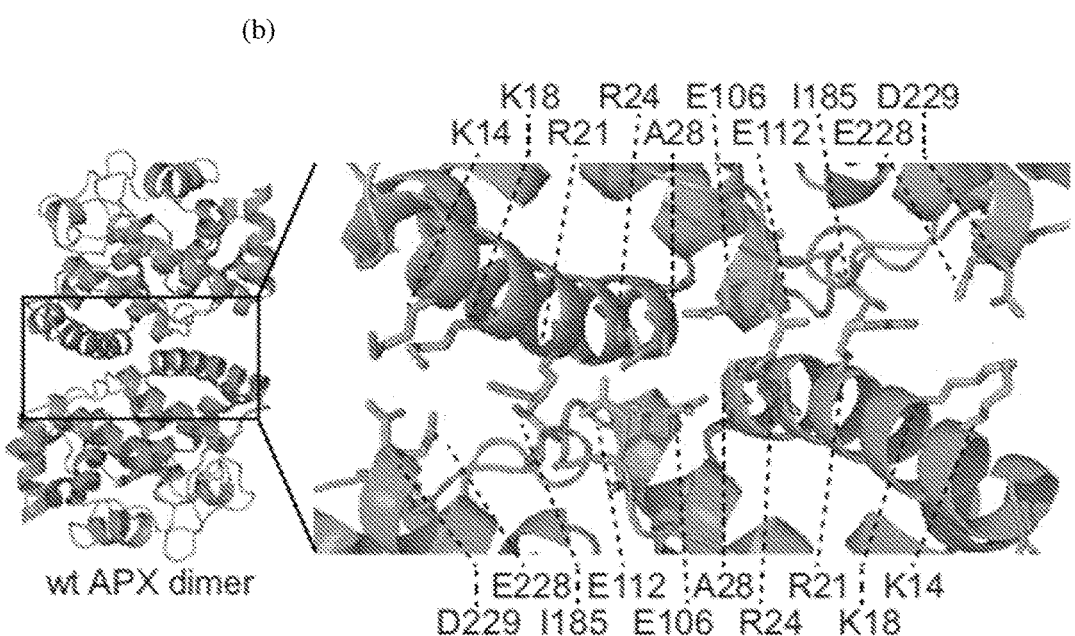
Figure 4:
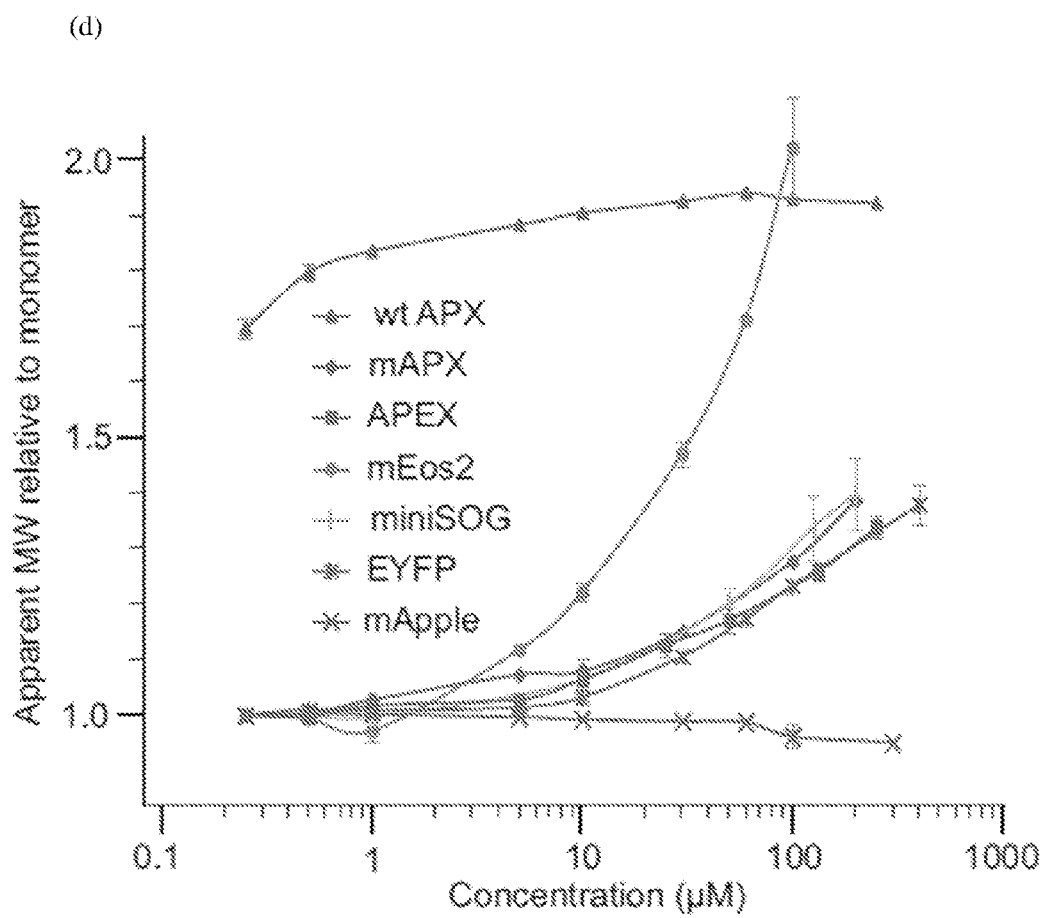

As shown in FIG. 4b, at least residues K14, K18, R21, R24, A28, E106, E112, I185, E228, and D229 in an exemplary APX (SEQ ID NO:1) may be involved in formation of the dimer interface of this enzyme. It is suggested that E17 and K20 may also be involved in dimer formation. Thus, a monomeric mutant of this APX can contain mutations (e.g., amino acid residue substitutions) at one or more of these positions. For example, the following amino acid residue substitution(s) can be introduced into SEQ ID NO:1 to produce a monomeric mutant: K14D, E17N, K20A, R21L, A28K, E112K, E228K, D229K, or a combination thereof (e.g., A28K/E112K, K14D/E228K, K14D/D229K, K14D/E112K, E112K/D229K, A28K/E112K/D229K, K14D/E112K/D229K, K14D/E112K/E228K, or A28K/E112K/E228K). Examples of monomeric mutants of SEQ ID NO:1 include, but are not limited to, single mutant K14D, A28K, E112K, E228K, or D229K, double mutant A28K/E112K, K14D/E112K (mAPX), K14D/E228K, K14D/D229K, E112K/E228K, or E112K/D229K, triple mutant E17N/K20A/R21L, A28K/E112K/D229K, K14D/W41F/E112K, K14D/E112K/D229K, K14D/E112K/E228K, or A28K/E112K/E228K.

As used herein, "single mutant," "double mutant," "triple mutant," "quadruple mutant," "quintuple mutant," etc. refer to mutants containing only the 1, 2, 3, 4, 5, etc. defined amino acid residue substitutions as compared to the corresponding wild-type counterpart. For example, double mutant K14D/E112K (also designated "mAPX" in the present disclosure) is a mutant that is otherwise identical to SEQ ID NO:1 except for the K14D and E112K substitutions and triple mutant K14D/W41F/E112K (APEX) is otherwise identical to SEQ ID NO:1 except for the three defined amino acid residue substitutions.

Monomeric mutants of other APX enzymes can contain one or more mutations (e.g., amino acid residue substitutions) at one or more positions involved in dimerization of the counterpart wild-type enzyme, e.g., corresponding to those in SEQ ID NO:1 as described above.

The same mutagenesis strategy as described above can be applied to BCPs to generate BCP monomeric mutants.

In other embodiments, the peroxidase mutants described herein are high activity mutants, i.e., exhibiting higher enzymatic activity (particularly towards a desirable substrate, such as DAB) as compared to their wild-type counterpart (e.g., having an enzymatic activity at least 20%, 50%, 1-fold, 2-fold, 3-fold, 5-fold, 10-fold, 20-fold, 50-fold, 100-fold, 1000-fold, or higher than the wild-type counterpart). Such a mutant can contain mutations (e.g., amino acid residue substitutions) at one or more positions involved in enzymatic activity (e.g., heme binding sites or substrate binding sites). In some examples, such a high activity mutant share at least 80% (e.g., 85%, 90%, 95%, or 98%) sequence homology to a wild-type reference peroxidase (e.g., an APX, a CCP, or a BCP).

Figure 5:
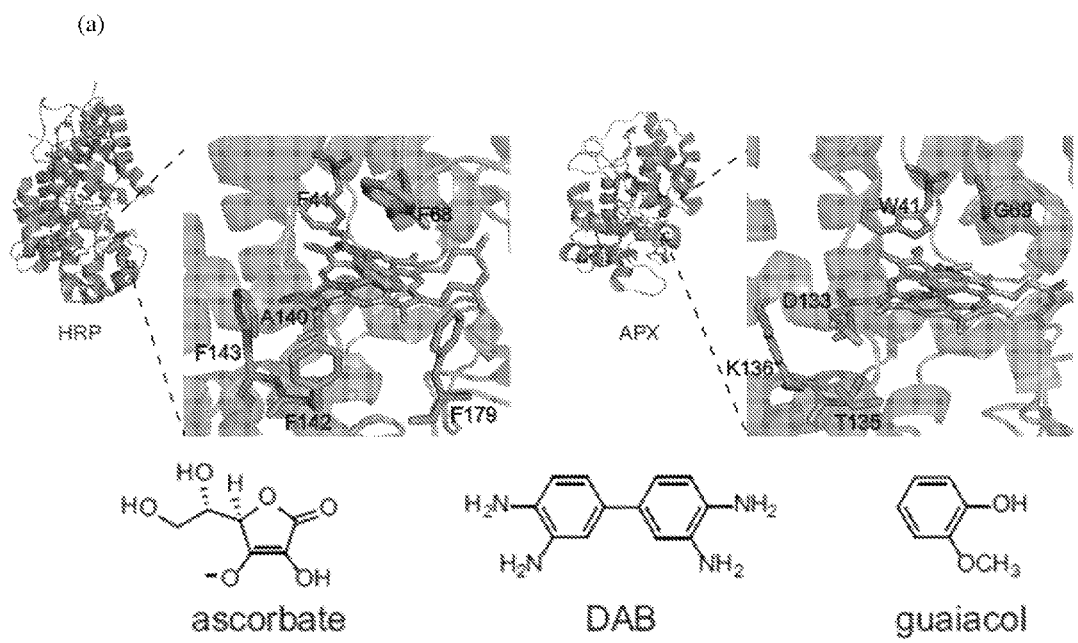
FIG. 5 is a diagram detailing the active-site engineering strategy used to boost the activity of APEX. (a) Comparison of the active sites of wt HRP and wt APX (from PDB IDs 1H5A29 and 1V0H30, respectively). The heme cofactor is shown in the middle of the magnified view for each enzyme. The co-crystallized substrate analogues (benzohydroxamic acid for HRP and salicylhydroxamic acid for APX) are shown directly above the heme cofactors. The HRP active site is lined with aromatic side chains, whereas the APX active site has only a single tryptophan at position 41. Chemical structures of ascorbate (the natural substrate of APX), DAB (the desired substrate for EM applications), and guaiacol are shown below. (b) Kinetic constants of wtAPX and APX mutants engineered to resemble HRP. kcat and KM values were measured using a spectrophotometric assay with guaiacol as substrate. (c) DAB polymerization activities of wt APX, mAPX, and APEX, expressed in the cytosol, in the absence or increasing presence of heme. For each condition, the mean fraction of transmitted light absorbed was calculated for >60 transfected cells, then averaged together.
Figure 5:
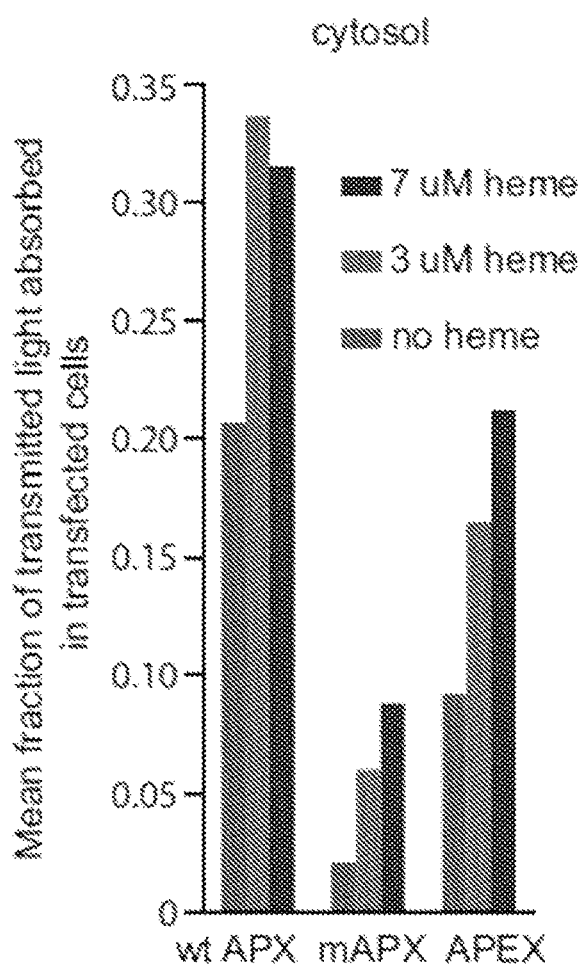

In some examples, a high activity mutant of APX can be prepared by transplanting features of the active site of HRP (which acts on DAB), e.g., the cage of hydrophobic (e.g., aromatic) sidechains, into a wild-type APX. As shown in FIG. 5a, W41, G69, D133, T135, and K136 in SEQ ID NO:1 may constitute the active site of a pea APX (SEQ ID NO:1). A high activity mutant of this APX can be prepared by replacing one or more of these residues with a hydrophobic (e.g., an aromatic residue such as F, Y, or W). For example, at least one of W41, G69, T135, and K136 can be replaced with F, Y, or W. Alternatively or in addition, D133 can be replaced with A, G, I, L, or V. Examples of high activity mutants of SEQ ID NO:1 can contain the following amino acid residue substitutions: W41F, G69F, W41F/G69F, D133A/T135F/K136F, W41F/D133A/T135F/K136F, G69F/D133A/T135F/K136F, and W41F/G69F/D133A/T135F/K136F.

High activity mutants of other APX enzymes can contain one or more mutations (e.g., amino acid residue substitutions) at one or more positions involved in enzymatic activity of the counterpart wild-type enzyme, e.g., corresponding to those in SEQ ID NO:1 as described above. In some examples, a hydrophobic residue (e.g., an aromatic residue) is introduced into one or more of the residues important to the enzymatic activity of the peroxidase, which can be identified by comparing the amino acid sequence of the wild-type enzyme with SEQ ID NO:1.

In other embodiments, high activity mutants of a CCP enzyme can be prepared by introducing mutations (e.g., amino acid residue substitutions) at one or more active sites of a reference yeast CCP, e.g., positions corresponding to W51, S81, D146, D148, K149, and G186 in SEQ ID NO:2. In some examples, one or more positions corresponding to W51, S81, D148, K149, and G186 in SEQ ID NO:2 are replaced with a hydrophobic residue (e.g., an aromatic residue such as F, Y, or W) to produce a high activity mutant. Alternatively or in addition, the residue at the position corresponding to D146 in SEQ ID NO:2 can be replaced with a hydrophobic residue such as A, G, V, I, and L.

In yet other embodiments, high activity mutants of a BCP enzyme can be prepared by introducing mutations (e.g., amino acid residue substitutions) at one or more active sites of a reference wild-type BCP, e.g., positions corresponding to W107, D137, E223, N231, and G316 in SEQ ID NO:3. In some examples, one or more positions corresponding to W107, D137, E223, and G316 in SEQ ID NO:3 are replaced with a hydrophobic residue (e.g., an aromatic residue such as F, Y, or W) to produce a high activity mutant. Alternatively or in addition, the residue at the position corresponding to N231 in SEQ ID NO:3 can be replaced with a hydrophobic residue such as A, G, V, I, and L.

Further, the Class I heme peroxidase mutants described herein can contain both one or more mutations leading to monomer formation and one or more mutations leading to elevated enzymatic activity. Such a mutant can contain any combination of the monomeric mutations and high activity mutations described herein. For example, such an APX mutant can contain a combination of (a) K14D, E112K, E228K, D229K, K14D/E112K, K14D/E228K, K14D/D229K, E17N/K20A/R21L, or K14D/W41F/E112K, and (b) G69F, G174F, W41F/G69F, D133A/T135F/K136F, W41F/D133A/T135F/K136F, G69F/D133A/T135F/K136F, or W41F/G69F/D133A/T135F/K136F. In some examples, the just-described APX mutant can be a combination of (a) single mutant K14D, single mutant E112K, single mutant E228K, single mutant D229K, double mutant K14D/E112K, double mutant K14D/E228K, double mutant K14D/D229K, triple mutant E17N/K20A/R21L, or triple mutant K14D/W41F/E112K, and (b) single mutant W41F, single mutant G69F, single mutant G174F, double mutant W41F/G69F, triple mutant D133A/T135F/K136F, quadruple mutant W41F/D133A/T135F/K136F, quadruple mutant G69F/D133A/T135F/K136F, or quintuple mutant W41F/G69F/D133A/T135F/K136F. Examples of such combined mutants include, but are not limited to, K14D/E112K/W41F (APEX), and K14D/E112K/W41F/D133A/T135F/K136F.

Any of the wild-type and mutated Class I heme peroxidases as described herein can be prepared by routine recombinant technology. In particular, mutants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. See also Example 1 below. Alternatively, mutations (e.g., conservative amino-acid substitutions in the amino acid sequence of a wild-type peroxidase) can be made by alteration of a nucleic acid encoding the wild-type enzyme. Such substitutions can be made by a variety of methods known to one of ordinary skill in the art. For example, amino acid substitutions may be made by PCR-directed mutation, site-directed mutagenesis according to the method of Kunkel (Kunkel, PNAS 82: 488-492, 1985), or by chemical synthesis of a nucleic acid molecule encoding a Class I heme peroxidase mutant.

Nucleic acids encoding a wild-type or mutated Class I heme peroxidase can be inserted via routine cloning technology into a vector, such as an expression vector in which the coding sequence is in operable linkage with a suitable promoter. As used herein, a "vector" may be a nucleic acid into which one or more desired sequences may be inserted by, e.g., restriction and ligation, for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector can be introduced into a suitable host cell and the transformed host cell thus obtained can be cultured under suitable conditions allowing expression of the wild-type or mutated Class I heme peroxidase. The expressed enzyme can then be isolated from the cell culture; its enzymatic activity and monomeric property can be confirmed via methods known in the art, e.g., SDS-PAGE, gel filtration, and an in vitro enzymatic assay. See also Examples below.

Use of Class I Heme Peroxidases as Reporters in Microscopy Imaging

Any of the Class I heme peroxidase, including any of the wild-type enzymes, monomeric mutants, high activity mutants, or combinations thereof as described herein, can be used in the imaging method described herein for determining, e.g., protein topology. In general, this imaging method can be performed by providing a sample containing cells that express a Class I heme peroxidase, a fusion protein comprising a Class I peroxidase, and a protein of interest, a cellular localization signal peptide, and/or a protein tag. This method is particularly useful in studying in live cells the structure/function of the protein of interest, which can be any protein, such as mammalian proteins.

This method is particularly useful in imaging cellular organelle (e.g., mitochondria) in live cells.

To perform the imaging methods described herein, a Class I heme peroxidase, either alone or in fusion with a protein of interest or a cellular localization signal peptide, is introduced into a host cell of interest for expression via routine recombinant technology. A protein of interest can be any protein, the topology of which is of interest. In some examples, a protein of interest can be a subcellular compartment-specific protein, such as a cytosol protein, mitochondrial protein, mitochondrial matrix protein, a mitochondrial intermembrane space protein, a mitochondrial inner membrane protein, a mitochondrial outer membrane protein (facing cytosol), a Golgi protein, an endoplasmic reticulum lumen protein, an endoplasmic reticulum membrane protein (facing cytosol), a cell surface protein, a secreted protein, a nuclear protein, a vesicle protein, a cell skeleton protein, a cell skeleton-binding protein, a motor protein, a gap junction protein, a chromatin-organizing protein, a transcription factor protein, a DNA polymerase protein, a ribosomal protein, a synaptic protein, or an adhesion protein.

Cellular localization signal peptides comprises amino acid sequence that recognize, target, or direct the polypeptide containing such to a particular sub-cellular component, e.g., the nucleus, cytoplasm, mitochondria, or Golgi apparatus. See: C. Dingwall et al. (1991) TIBS 16:478-481. Such signal peptides are well known in the art. See, e.g., Snapp et al., 2003, J. Cell Biol., 163(2):257-269; Perocchi et al., 2010, Nature, 467:291-297; and Uttamapinant et al., 2010, PNAS 107(24):10914-10919. Cellular localization signal peptides for use in the present disclosure include, but are not limited to, nuclear export signals (NES), nuclear localization signals (NLS), matrix signals, ER localization/targeting signals, mitochondrial-targeting signals, and Golgi-targeting signals. Examples are, but are not limited to, DPVVVLGL-CLSCLLLLSLWKQSYGGG (SEQ ID NO:4) (ER), MLA-TRVFSLVGKRAISTSVCVRAH (SEQ ID NO:5) (mitochondria), LQLPPLERLTLD (SEQ ID NO:6) (nuclear export signal, cytosyl), and KDEL (SEQ ID NO:7) (ER/Golgi), and functional variants thereof, e.g., containing mutations such as conservative amino acid residue substitutions at one or more positions (e.g., up to 2, 3, 4, or more positions). See also Table 3 below.

A Class I heme peroxidase or a fusion protein containing such can be further fused in frame with a protein tag, which can be any of those routinely used in fusion technology (e.g., Flag and c-Myc) to facilitate protein expression, detection, and/or purification. A protein tag is a peptide sequence genetically grafted onto the enzyme or the fusion protein for various purposes, e.g., affinity purification (affinity tag), enhancing solubilization (solubilication tag), or facilitating chromatography (chromatography tag) or detection (epitope or fluorescence tag). Affinity tags include chitin binding protein (CBP), maltose binding protein (MBP), glutathione-S-transferase (GST), and poly(His) tag. Solubilization tags include thioredoxin (TRX), poly(NANP) (SEQ ID NO:14), MBP, and GST. Chromatography tags include those consisting of polyanionic amino acids, such as FLAG-tag. Epitope tags include short peptide sequences derived from viral genes, such as V5-tag, c-myc-tag, and HA-tag. Fluorescence tags include GFP and its variants.

When necessary, a coding sequence for a Class I heme peroxidase can be subjected to codon optimization based on the type of host cells, in which the enzyme is to be expressed. For example, when the enzyme is to be expressed in a mammalian cell, its coding sequence can be subjected to codon optimization using optimal mammalian codons.

A nucleic acid encoding a Class I heme peroxidase or a fusion protein containing such can be inserted into a suitable expression vector in operable linkage to a suitable promoter. An expression vector is one into which a desired DNA sequence may be inserted by restriction and ligation such that it is operably joined to regulatory sequences and may be expressed as an RNA transcript. Vectors may further contain one or more marker sequences (i.e., reporter sequences) suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., beta-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, a marker or coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CCAAT sequence, and the like. Especially, such 5' non-transcribed regulatory sequences will include a promoter region which includes a promoter sequence for transcriptional control of the operably joined coding sequence. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous nucleic acid, usually DNA, molecules, encoding a Class I heme peroxidase. The heterologous nucleic acid molecules are placed under operable control of transcriptional elements to permit the expression of the heterologous nucleic acid molecules in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (Nuc. Acids Res. 18:5322, 1990), and its use in transfection experiments is disclosed by, for example, Demoulin (Mol. Cell. Biol. 16:4710-4716, 1996).

Still another preferred expression vector is an adenovirus, described by Stratford-Perricaudet, which is defective for E1 and E3 proteins (J. Clin. Invest. 90:626-630, 1992). The use of the adenovirus as an Adeno.P1A recombinant is disclosed by Warnier et al., in intradermal injection in mice for immunization against P1A (Int. J. Cancer, 67:303-310, 1996).

In some embodiments, the expression of a Class I heme peroxidase or a fusion protein thereof can be under the control of a cell type/cell tissue-specific promoter which drives the expression of a target protein in a specific type of cells. This is particularly useful, among others, for imaging a particular type of cells in a tissue sample.

Tissue-specific and/or cell type-specific promoters include, but are not limited to, the albumin promoter (e.g., liver-specific albumin promoter; see Pinkert et al. (1987) Genes Dev 1:268-277); lymphoid-specific promoters (Calame and Eaton (1988) Adv Immunol 43:235-275), such as promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748); neuron-specific promoters (e.g., the neurofilament promoter; see Byrne and Ruddle (1989) PNAS 86:5473-5477); pancreas-specific promoters (Edlund et al. (1985) Science 230:912-916); mammary gland-specific promoters (e.g., milk whey promoter; see U.S. Pat. No. 4,873, 316 and European Application Publication No. 264,166); and developmentally regulated promoters, e.g., the murine hox promoters (Kessel and Gruss (1990) Science 249:374-379) and the alpha-fetoprotein promoter (Campes and Tilghman (1989) Genes Dev 3:537-546).

Cells expressing the Class I heme peroxidase or a fusion protein containing such, can be prepared by routine molecular and cell biology techniques. Either live or fixed cells can be incubated with a peroxidase substrate for a suitable period of time to allow the substrate to be converted into a signal-releasing product such as a polymer or a fluorescent dye via an oxidation reaction catalyzed by the peroxidase. Suitable substrates of the Class I heme peroxidase, e.g., an APX, are well known in the art. For example, an APX can act on ascorbate and other aromatic substrates (e.g., gualacol and salicylhydroxamic acid). In some examples, the Class I heme peroxidase substrates for use in the imaging method described herein is diaminobenzidine (DAB; including any isoform thereof) or a DAB analog (e.g., 4-chloro-1-naphthol or 3-amino-9-ethylcarbazole; Krieg et al., 2000, Cell Mol. Biol. 46(7):1191-1212; and Baskin et al., 1982, J. Histochemistry & Cytochemistry, 30(7):710-712). In other examples, the substrate is a phenol or an aniline.

As used herein, a phenol is a phenyl moiety that is substituted with one or more —OH, one or more —O$^-$, and/or one or more —OH$_2^+$ groups. The phenyl moiety may be further substituted with other substituents including, but not limited to, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A1}$, —N(R$^{A1}$)$_2$, —SR$^{A1}$, —CN, —C(=NR$^{A1}$)R$^{A1}$, —C(=NR$^{A1}$)OR$^{A1}$, —C(=NR$^{A1}$)SR$^{A1}$, —C(=NR$^{A1}$)N(R$^{A1}$)$_2$, —C(=S)R$^{A1}$, C(=S)OR$^{A1}$, —C(=S)SR$^{A1}$, —C(=S)N(R$^{A1}$)$_2$, —NO$_2$, —N$_3$, —N(R$^{A1}$)$_3^+$F$^-$, —N(R$^{A1}$)$_3^+$Cl$^-$, —N(R$^{A1}$)$_3^+$Br$^-$, —N(R$^{A1}$)$_3^+$I$^-$, —N(OR$^{A1}$)R$^{A1}$, —NR$^{A1}$C(=O)R$^{A1}$, —NR$^{A1}$C(=O)OR$^{A1}$, —NR$^{A1}$C(=O)SR$^{A1}$, —NR$^{A1}$C(=O)N(R$^{A1}$)$_2$, —NR$^{A1}$C(=S)R$^{A1}$, —NR$^{A1}$C(=S)OR$^{A1}$, —NR$^{A1}$C(=S)SR$^{A1}$, —NR$^{A1}$C(=S)N(R$^{A1}$)$_2$, —NR$^{A1}$C(=NR$^{A1}$)R$^{A1}$, —NR$^{A1}$C(=NR$^{A1}$)OR$^{A1}$, —NR$^{A1}$C(=NR$^{A1}$)SR$^{A1}$, —NR$^{A1}$C(=NR$^{A1}$)N(R$^{A1}$)$_2$, —NR$^{A1}$S(=O)$_2$R$^{A1}$, —NR$^{A1}$S(=O)$_2$OR$^{A1}$, —NR$^{A1}$S(=O)$_2$SR$^{A1}$, —NR$^{A1}$S(=O)$_2$N(R$^{A1}$)$_2$, —NR$^{A1}$S(=O)R$^{A1}$, —NR$^{A1}$S(=O)OR$^{A1}$, —NR$^{A1}$S(=O)SR$^{A1}$, —NR$^{A1}$S(=O)N(R$^{A1}$)$_2$, —NR$^{A1}$P(=O), —NR$^{A1}$P(=O)$_2$, —NR$^{A1}$P(=O)(R$^{A1}$)$_2$, —NR$^{A1}$P(=O)R$^{A1}$(OR$^{A1}$), —NR$^{A1}$P(=O)(OR$^{A1}$)$_2$, —OC(=O)R$^{A1}$, —OC(=O)OR$^{A1}$, —OC(=O)SR$^{A1}$, —OC(=O)N(R$^{A1}$)$_2$, —OC(=NR$^{A1}$)R$^{A1}$, —OC(=NR$^{A1}$)OR$^{A1}$, —OC(=NR$^{A1}$)N(R$^{A1}$)$_2$, —OC(=S)R$^{A1}$, —OC(=S)OR$^{A1}$, —OC(=S)SR$^{A1}$, —OC(=S)N(R$^{A1}$)$_2$, —ON(R$^{A1}$)$_2$, —OS(=O)R$^{A1}$, —OS(=O)OR$^{A1}$, —OS(=O)SR$^{A1}$, —OS(=O)N(R$^{A1}$)$_2$, —OS(=O)$_2$R$^{A1}$, —OS(=O)$_2$OR$^{A1}$, —OS(=O)$_2$SR$^{A1}$, —OS(=O)$_2$N(R$^{A1}$)$_2$, —OP(=O)(R$^{A1}$)$_2$, —OP(=O)R$^{A1}$(OR$^{A1}$), —OP(=O)(OR$^{A1}$)$_2$, —S(=O)R$^{A1}$, —S(=O)OR$^{A1}$, —S(=O)N(R$^{A1}$)$_2$, —S(=O)$_2$R$^{A1}$, —S(=O)$_2$OR$^{A1}$, —S(=O)$_2$N(R$^{A1}$)$_2$, —SC(=O)R$^{A1}$, —SC(=O)OR$^{A1}$, —SC(=O)SR$^{A1}$, —SC(=O)N(R$^{A1}$)$_2$, —SC(=S)R$^{A1}$, —SC(=S)OR$^{A1}$, —SC(=S)SR$^{A1}$, —SC(=S)N(R$^{A1}$)$_2$, —P(=O)(R$^{A1}$)$_2$, —P(=O)(OR$^{A1}$)$_2$, —P(=O)R$^{A1}$(OR$^{A1}$), and —P(=O)$_2$, wherein each occurrence of R$^{A1}$ is independently selected from the group consisting of hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, and a sulfur protecting group when attached to a sulfur atom, or two R$^{A1}$ groups are joined to form an optionally substituted heterocyclic ring. An example of phenol is hydroxybenzene.

As used herein, an aniline is a phenyl moiety that is substituted with one or more —NH$_2$, one or more —NH$_{3+}$, and/or one or more —NH$^-$ groups. The phenyl moiety may be further substituted with other substituents including, but not limited to, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B1}$, —N(R$^{B1}$)$_2$, —SR$^{B1}$, —CN, —C(=NR$^{B1}$)R$^{B1}$, —C(=NR$^{B1}$)OR$^{B1}$, —C(=NR$^{B1}$)SR$^{B1}$, —C(=NR$^{B1}$)N(R$^{B1}$)$_2$, —C(=S)R$^{B1}$, —C(=S)OR$^{B1}$, —C(=S)SR$^{B1}$, —C(=S)N(R$^{B1}$)$_2$, —NO$_2$, —N$_3$, —N(R$^{B1}$)$_3^+$F$^-$, —N(R$^{B1}$)$_3^+$Cl$^-$, —N(R$^{B1}$)$_3^+$Br$^-$, —N(R$^{B1}$)$_3^+$I$^-$, —N(OR$^{B1}$)R$^{B1}$, —NR$^{B1}$C(=O)R$^{B1}$, —NR$^{B1}$C(=O)OR$^{B1}$, —NR$^{B1}$C(=O)SR$^{B1}$, —NR$^{B1}$C(=O)N(R$^{B1}$)$_2$, —NR$^{B1}$C(=S)R$^{B1}$, —NR$^{B1}$C(=S)OR$^{B1}$, —NR$^{B1}$C(=S)SR$^{B1}$, —NR$^{B1}$C(=S)N(R$^{B1}$)$_2$, —NR$^{B1}$C(=NR$^{B1}$)R$^{B1}$, —NR$^{B1}$C(=NR$^{B1}$)OR$^{B1}$, —NR$^{B1}$C(=NR$^{B1}$)SR$^{B1}$, —NR$^{B1}$C(=NR$^{B1}$)N(R$^{B1}$)$_2$, —NR$^{B1}$S(=O)$_2$R$^{B1}$, —NR$^{B1}$S(=O)$_2$OR$^{B1}$, —NR$^{B1}$S(=O)$_2$SR$^{B1}$, —NR$^{B1}$S(=O)$_2$N(R$^{B1}$)$_2$, —NR$^{B1}$S(=O)R$^{B1}$, —NR$^{B1}$S(=O)OR$^{B1}$, —NR$^{B1}$S(=O)SR$^{B1}$, —NR$^{B1}$S(O)N(R$^{B1}$)$_2$, —NR$^{B1}$P(=O), —NR$^{B1}$P(=O)$_2$, —NR$^{B1}$P(=O)(R$^{B1}$)$_2$, —NR$^{B1}$P(=O)R$^{B1}$(OR$^{B1}$), —NR$^{B1}$P(=O)(OR$^{B1}$)$_2$, —OC(=O)R$^{B1}$, —OC(=O)OR$^{B1}$, —OC(=O)SR$^{B1}$, —OC(=O)N(R$^{B1}$)$_2$, —OC(=NR$^{B1}$)R$^{B1}$, —OC(=NR$^{B1}$)OR$^{B1}$, —OC(=NR$^{B1}$)N(R$^{B1}$)$_2$, —OC(=S)R$^{B1}$, —OC(=S)OR$^{B1}$, —OC(=S)SR$^{B1}$, —OC(=S)N(R$^{B1}$)$_2$, —ON(R$^{B1}$)$_2$, —OS(=O)R$^{B1}$, —OS(=O)OR$^{B1}$, —OS(=O)SR$^{B1}$, —OS(=O)N(R$^{B1}$)$_2$, —OS(=O)$_2$R$^{B1}$, —OS(=O)$_2$OR$^{B1}$, —OS(=O)$_2$SR$^{B1}$, —OS(=O)$_2$N(R$^{B1}$)$_2$, —OP(=O)(R$^{B1}$)$_2$, —OP(=O)R$^{B1}$(OR$^{B1}$), —OP(=O)(OR$^{B1}$)$_2$, —S(=O)R$^{B1}$, —S(=O)OR$^{B1}$, —S(=O)N(R$^{B1}$)$_2$, —S(=O)$_2$R$^{B1}$, —S(=O)$_2$OR$^{B1}$, —S(=O)$_2$N(R$^{B1}$)$_2$, —SC(=O)R$^{B1}$, —SC(=O)OR$^{B1}$, —SC(=O)SR$^{B1}$, —SC(=O)N(R$^{B1}$)$_2$, —SC(=S)R$^{B1}$, —SC(=S)OR$^{B1}$, —SC(=S)SR$^{B1}$, SC(=S)N(R$^{B1}$)$_2$, —P(=O)(R$^{B1}$)$_2$, —P(=O)(OR$^{B1}$)$_2$, —P(=O)R$^{B1}$(OR$^{B1}$), and —P(=O)$_2$, wherein each occurrence of R$^{B1}$ is independently selected from the group consisting of hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, and a sulfur protecting group when attached to a sulfur atom, or two R$^{B1}$ groups are joined to form an optionally substituted heterocyclic ring. An example of aniline is aminobenzene.

Examples of the peroxidase substrates for use in the imaging method described herein include, but are not limited to, those listed in Table 2 below:

TABLE 2

Exemplary Peroxidase Substrates

| Compound | classification |
|---|---|
| 4-chloro-1-naphthol, | Phenol |
| Guaiacol | Phenol |
| Pyrogallol | Phenol |
| Amplex UltraRed | phenol |
| Dihydrofluorescin | Phenol |
| p-cresol | phenol |
| Dopamine | Phenol |
| 3-methylphenol | Phenol |
| 4-methoxyphenol | Phenol |
| 4-hydroxybenzaldehyde | Phenol |
| 3-amino-9-ethylcarbazole, | Aniline |
| DAB | Aniline |
| o-phenylenediamine, | Aniline |
| 3,3',5,5'-tetramethylbenzidine, | Aniline |
| o-diansidine, | Aniline |
| Luminol | Aniline |
| 4-aminophthalhydrazide | Aniline |
| N-(6-Aminohexyl)-N-ethylisoluminol | Aniline |
| N-(4-Aminobutyl)-N-ethylisoluminol | Aniline |
| 3-methylaniline | Aniline |
| 4-methylaniline | Aniline |
| 4-methoxyaniline | Aniline |
| 5-aminosalicylic acid, | Both aniline and phenol |
| 3-methyl-2-benzothiazolinone hydrazone | neither |
| 2,2'-azino-bis(3-Ethylbenzthiazoline-6-Sulfonic Acid) | (neither) |

The substrate compounds described herein can be obtained from commercial vendors, e.g., Sigma Aldrich. Alternatively, they can be synthesized by chemistry transformations (including protecting group methodologies), e.g., those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

Cells expressing a Class I heme peroxidase, either live or fixed, can be incubated with a suitable substrate under suitable conditions for a suitable period to allow conversion of the substrate into a product that releases a detectable signal, which can then be examined under a microscope (e.g., an electron microscope) for imaging following routine techniques. See, e.g., Shu et al., PLos Biol. 2011, 9(4): e1001041. Utilizing a Class I heme peroxidase such as APEX described herein provides the opportunity not only for EM contact, but also for colorimetric, fluorescent, and chemiluminescent readouts.

In one example, a Class I heme peroxidase (e.g., APEX) fused with a protein of interest is expressed in live cells (e.g., mammalian cells). After expression, the cells can be fixed, and then incubated in a solution of DAB. H$_2$O$_2$, can then added into the mixture to allow the Class I heme peroxidase, which retains activity in fixative, to catalyzes the oxidative reaction, resulting in polymerization of DAB to generate a cross-linked precipitate. The cells carrying the DAB polymer thus produced can then be incubated with electron-dense OsO4 to generate EM contrast.

Other Utilities of Class I Heme Peroxidase Mutants

In addition to microscopy imaging, any of the Class I heme peroxidase mutants described herein can also be used for various other purposes, including bioremediation, biocatalysis, diagnostics, biosensors, protein expression, transgenics, bioinformatics, protein engineering, and medical treatment. Processes for performing these uses are well known in the art. See, e.g., Ryan et al., 2006, Trends in Biotechnology, 24(8):355-363.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1

Generation and Characterization of Ascorbate Peroxidase Mutants

Materials and Methods

Cloning and Mutagenesis of APX Plasmids

The pTRC99A expression vector encoding pea cytosolic APX with a His$_6$-tag appended to its N-terminus has been described previously (Cheek, et. al., Journal of Biological Inorganic Chemistry 4, 64-72. (1999)). This gene was originally derived from a pea leaf (Pisum sativum L.) cDNA library (Patterson, et. al., Journal of Biological Chemistry 269, 17020-17024 (1994)) and encodes the following amino acid sequence for APX:

```
                                           (SEQ ID NO: 22)
RGKSYPTVSPDYQKAIEKAKRKLRGFIAEKKCAPLILRLAWHSAGTFDS

KTKTGGPFGTIKHQAELAHGANNGLDIAVRLLEPIKEQFPIVSYADFYQ

LAGVVAVEITGGPEVPFHPGREDKPEPPPEGRLPDATKGSDHLRDVFG

KAMGLSDQDIVALSGGHTIGAAHKERSGFEGPWTSNPLIFDNSYFTEL

LTGEKDGLLQLPSDKALLTDSVFRPLVEKYAADEDVFFADYAEAHLKL

SELGFAEA
```

Mutants of pea APX, including K14D, E112K, E228K, D229K, K31S, A233D, I185K, A28K, A28K/E112K, K14D/E112K, K14D/E228K, K14D/D229K, E112K/E228K, E17N/K20A/R21L, W41F, G69F, G174F, W41F/G69F, D133A/T135F/K136F, D133A/T135F/K136F/W41F, D133A/T135F/K136F/G69F, D133A/T135F/K136F/W41F/

G69F, E112K/D229K, A28K/E112K/D229K, K14D/E112K/D229K, K14D/E112K/E228K, A28K/E112K/E228K were generated using standard molecular biology techniques, such as QuikChange mutagenesis (Stratagene) or overlap extension PCR33. The pTRC plasmids containing mutants of APX were used directly for bacterial expression. Some mutants were subcloned into the pET21a (EMD Chemicals) expression vector between the NdeI and XhoI restriction sites, which enabled higher protein yield than pTRC. Fusions of APX to mammalian proteins and localization signals were generated using standard restriction cloning methods. Table 2 below presents an overview of all mammalian expression constructs used in this study.

TABLE 3

Summary of Genetic Constructs

| Name | Features | Variants | Details |
|---|---|---|---|
| APEX-NES in pcDNA3 | NheI-Flag-APEX-NES-Stop-EcoRI | wt APX, mAPX, APX$^{W41F}$, HRP* | Flag: DYKDDDDK (SEQ ID NO: 8)<br>NES: LQLPPLERLTLD (SEQ ID NO: 6) |
| APEX-NLS in pcDNA3 | NotI-Flag-APEX-EcoRI-NLS-Stop-XhoI | wt APX, mAPX | NLS: PKKKRKVDPKKKRKVDPKKKRKV (SEQ ID NO: 9) |
| Mito matrix-APEX in pcDNA3 | NotI-matrix-BamHI-APEX-Flag-Stop-XhoI | wt APX, mAPX, mAPX + FFAF**, HRP* | Matrix: MLATRVFSLVGKRAISTSVCVRAH (SEQ ID NO: 5)<br>Sequence is derived from COX4 |
| APEX-ER lumen in pDisplay | EcoRI-Ig k-chain ss-BglII-Flag-APEX-KDEL-Stop-AscI | wt APX, mAPX, HRP* | Ig k-chain ss: METDTLLLWVLLLWVPGSTGD (SEQ ID NO: 15)<br>ER localization sequence: KDEL (SEQ ID NO: 7) |
| Connexin43-GFP-APEX in pcDNA3 | HindIII-Cx43-BamHI-GGGGS linker-GFP-AscI-10 aa linker-APEX-Stop-XhoI | wt APX, mAPX | Derived from rat connexin43-GFP-4Cys<br>10 aa linker: KGSGSTSGSG (SEQ ID NO: 16) |
| Connexin43-APEX in pcDNA3 | HindIII-Cx43-BamHI-10 aa linker-APEX-NotI-c-myc-Stop-XhoI | mAPX + FFAF** | c-myc: EQKLISEEDL (SEQ ID NO: 10)<br>10 aa linker: KGSGSTSGSG (SEQ ID NO: 16) |
| Connexin43-mCherry-APEX in pcDNA3 | HindIII-Cx43-BamHI-GGGGS linker-mCherry-10 aa linker-AgeI-APEX-c-myc-Stop-XhoI | | APEX is mammalian codon optimized<br>10 aa linker: KGSGSTSGSG (SEQ ID NO: 16) |
| Connexin43-APEX-mCherry in pcDNA3 | HindIII-Cx43-BamHI-GGGGS linker-APEX-10 aa linker-AgeI-mCherry-c-myc-Stop-XhoI | | APEX is mammalian codon optimized<br>10 aa linker: KGSGSTSGSG (SEQ ID NO: 16) |
| Vimentin-APEX in pECFP (Clontech) | EcoRI-vimentin-BamHI-4 aa linker-APEX-Flag-Stop-NotI | | Derived from human vimentin-mApple<br>4 aa linker: PVAT (SEQ ID NO: 17) |
| APEX-Histone2B in pEGFP (Clontech) | NheI-Flag-APEX-3 aa linker-BglII-5 aa linker-H2B-Stop-BamHI | | Derived from miniSOG-human H2B<br>10 aa linker (including BglII): SGLRSGGSGG (SEQ ID NO: 18) |
| MCU-APEX in pcDNA3 | NotI-MCU ss-MCU-linker-BamHI-V5-APEX-Stop-XhoI | C32A within APEX | Derived from human MCU-Flag. APEX is mammalian codon optimized.<br>V5: GKPIPNPLLGLDST (SEQ ID NO: 11)<br>Linker: CPTFLYKVVDLEGPRFE (SEQ ID NO: 19) |
| APEX-MCU in pcDNA3 | NotI-MCU ss-EcoRI-Flag-APEX-NheI-10 aa linker-MCU-Stop-XhoI | C32A within APEX, tdAPX$^{W41F}$, miniSOG | Derived from Flag-human MCU<br>APEX is mammalian codon optimized. 10 aa linker: GGSGGSGGSR (SEQ ID NO: 20) |

TABLE 3-continued

Summary of Genetic Constructs

| Name | Features | Variants | Details |
| --- | --- | --- | --- |
| IMS-sbAPEX in pcDNA3 | NotI-IMS ss-BamHI-V5-sbAPEX-Stop-XhoI | | IMS localization sequence: MYRLLSSVTARAAATAGPAWDGGRRG AHRRPGLPVLGLGWAGGLGLGLGLAL GAKLVVGLRGAVPIQS (SEQ ID NO: 21) sbAPEX is derived from soybean rather than pea ascorbate peroxidase |

*HRP: horseradish peroxidase.
**FFAF: D133A + T135F + K136F

APX Expression and Purification

N-terminally $His_6$-tagged APX and its mutants were expressed from pET21a or pTRC expression vectors in the BL21-DE3 strain of *Escherichia coli*. The pET21a vector gave significantly higher yield of APX, but a low percentage of heme incorporation (as determined by $A_{405}/A_{280}$), while pTRC gave a lower yield of APX with a high percentage heme incorporation. Individual colonies were amplified in 500 mL Luria Broth (LB) supplemented with 10 µg/mL ampicillin and grown to an O.D.$_{600}$ of 0.6 at 37° C. Protein expression was then induced with 420 µM isopropyl β-D-1-thiogalactopyranoside (IPTG) overnight at room temperature. Cells were harvested by centrifugation at 6400 g and lysed using B-PER (Bacterial Protein Extraction Reagents, Pierce) with 1 mM PMSF and protease inhibitor cocktail (Sigma), then centrifuged at 11000 g. The supernatant was allowed to incubate with 1.5 mL Ni-NTA agarose slurry (Qiagen) for 30 min. The APX-bound resin was loaded onto an Econo-Pac column (Bio-Rad) using gravity flow at 4° C. The resin was washed extensively, and APX was eluted in buffer containing 200 mM imidazole, then dialyzed extensively (3×4 L) at 4° C. in phosphate buffered saline (PBS), pH 7.4. When required, samples were concentrated using an Amicon Ultra-4 filter with Ultracel-10 membrane (Millipore). Purity was checked using SDS-PAGE. Protein samples were flash frozen in liquid $N_2$ and placed at −80° C. for long-term storage.

Heme Addition to Peroxidases

The heme occupancy of APX samples purified from *E. coli* was determined using the BCA assay for protein concentration and $\epsilon_{403}=1.14\times10^5$ $M^{-1}$ $cm^{-1}$ for heme concentration (Barrows, et. al., Biochemistry 44, 14062-14068 (2005)). Holo-APX concentration was determined based on protein content, which was measured using the Pierce BCA assay (Thermo Scientific). In cases when $A_{403}/A_{280}$ of an APX sample was <2.0, heme reconstitution was carried out according to the procedure of Cheek et. al. (*Journal of Biological Inorganic Chemistry* 4, 64-72. (1999)). Fractions containing reconstituted APX were identified by absorbance at 280 nm, then concentrated at 4° C. and exchanged into PBS buffer (3×4 mL) using an Amicon Ultra-4 filter with Ultracel-10 membrane (Millipore). Reconstituted APX samples with $A_{403}/A_{280}$>2.0 were deemed pure[34], and purity was confirmed by 16% SDS-PAGE.

Gel Filtration Chromatography

APX, fluorescent protein, or miniSOG preparations were diluted to the desired concentrations using chilled (4° C.) PBS and then allowed to incubate at room temperature for 30 min to overnight. Samples (100 µL) were run on a Waters HPLC system over a Superdex 75 10/300 column (GE Healthcare) that had been pre-equilibrated in PBS, pH 7.4. Samples were run isocratically in PBS at a flow rate of 0.5 mL/min. Elution of APX was monitored at 280 nm and 405 nm (heme absorbance). Empower software (Waters) was used for analysis of elution profiles. Apparent MWs were determined against low molecular weight standards (GE). For proteins that exhibited no significant change in apparent MW between 0.25 and 1 µM, the apparent MW of the monomer was estimated to be equal to the apparent MW at 0.25 µM. This estimation was applied for all proteins in FIG. 4d except wt APX, which was predominantly dimeric at 0.25 µM. The apparent MW of the monomer for wt APX was assumed to be equal to the apparent MW of mAPX at 0.25 µM.

Guaiacol Activity Assay

High activity toward guaiacol generally correlated well with robust polymerization of DAB in vitro. Guaiacol assays were performed on a Nanodrop 2000c UV-vis spectrophotometer (Thermo Scientific) using its cuvette reader. HRP (Sigma) was prepared as a 10 µM stock in PBS, flash frozen and stored at −80° C., and thawed immediately before use. Guaiacol peroxidase activity was measured according to the protocol of Lad et. al.[35] Oxidation to tetraguaiacol was monitored by absorbance at 470 nm ($\epsilon_{470}=22\times10^3$ $M^{-1}$ $cm^{-1}$). $K_{cat}$ and $K_M$ were calculated by nonlinear regression fitting to the Michaelis-Menten equation using OriginPro (OriginLab Corporation). All values are reported as the mean±standard deviation for 2-3 independent Michaelis-Menten fittings, with each fitting using at least 5 values of substrate concentration ranging between 0.25 and 30 mM.

In Vitro Characterization of Peroxidase Activity Toward DAB and Amplex Red

A solution of DAB (0.5 mg/mL) with 0.03% $H_2O_2$ in ice-cold 10 mM PBS was placed in a disposable cuvette and recorded as a blank on a UV/vis spectrometer. Absorbance at 370 nm was monitored for 1 min. Then a solution of purified enzyme in 10 mM PBS was added to the cuvette, and the solution was quickly mixed. Polymerization of DAB was detected by an increase in absorbance at 370 nm.

A solution of Amplex Red (50 uM) with 0.03% $H_2O_2$ in 10 mM PBS was mixed with a solution of purified enzymes in 10 mM PBS on a 96-well plate. The plate was quickly moved to a platereader, and peroxidase activity was monitored by the appearance of resorufin fluorescence (excitation 571 nm, emission 585 nm).

Mammalian Cell Culture and Transfection

HEK293T, Hela, and COS-7 cells were cultured as a monolayer in Minimum Essential Medium (MEM, Cellgro) supplemented with 10% fetal bovine serum (PAA Laboratores). Cells were maintained at 37° C. under an atmosphere of 5% $CO_2$. For imaging experiments, cells were grown either on 150 µm thickness glass coverslips or poly-d-lysine coated glass bottom dishes (P35GC-0-14-C, MatTek Corp.).

COS-7 cells were grown directly on glass. HEK293T cells were grown on glass pretreated with 50 g/mL fibronectin (Millipore). At 60-90% confluence, cells were transfected using Lipofectamine-2000 (Life Technologies) according to the manufacturer's instructions. Cells were fixed or labeled 18-24 h after transfection. For incubation of HEK293T cells with heme, the media was supplemented with a heme-bovine serum albumin (BSA) complex as previously described (Kremer, et. al., *Journal of Structural Biology* 116, 71-76 (1996)).

Results

Wild-Type and Monomeric APX were Active Throughout the Cell

Figure 7:
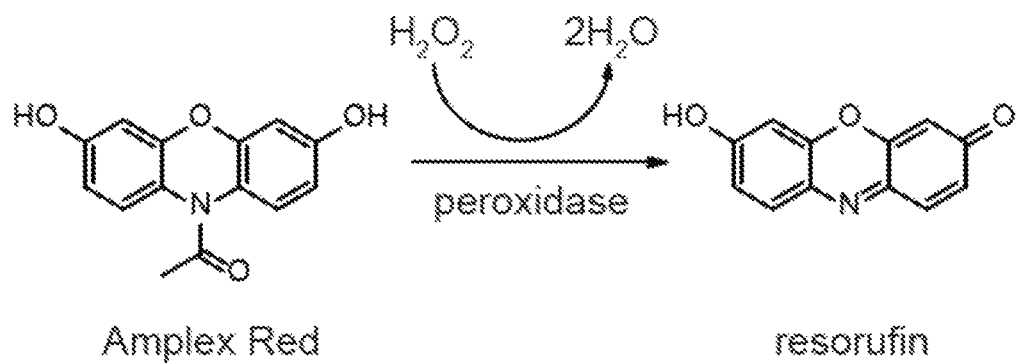
FIG. 7 shows the enzymatic reaction where resorufin, a fluorescent product, is produced from Amplex UltraRed (proprietary derivative of Amplex Red) through the action of a peroxidase in the presence of $H_2O_2$.

The expression and activity of wild-type (wt) APX was tested using immunostaining and Amplex UltraRed, a fluorogenic peroxidase substrate, in three cellular compartments: cytosol, mitochondrial matrix, and endoplasmic reticulum (ER). APX was differentially expressed in each compartment using at least the constructs described in Table 3. For comparison, HRP was tested in the same locations. Activity was monitored through visualization of resorufin, the fluorescent product of Amplex UltraRed oxidation by HRP or APX (scheme in FIG. 7). Both HRP and APX expressed in all three contexts, but HRP was inactive in the cytosol and mitochondrial matrix, while APX was active in all contexts. When live cells were imaged immediately after Amplex UltraRed labeling, resorufin fluorescence was seen throughout the entire cell. After fixation, however, the majority of the resorufin diffused out of the cells, and resorufin fluorescence remained only in the compartment in which APX was expressed. (Note that Amplex UltraRed, a proprietary derivative of Amplex Red, was used rather than Amplex Red in this example).

Figure 8:
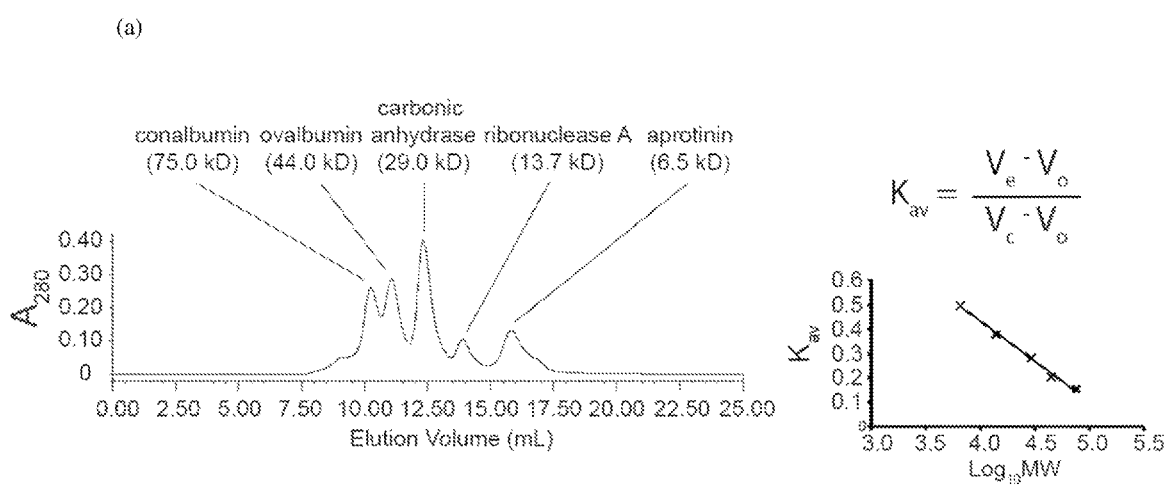
FIG. 8 is a diagram showing the analysis of APX and fluorescent protein variants by gel filtration chromatography (GFC). (a) (left) Gel filtration trace for the molecular weight standards used for calibration. (right) Derivation of $K_{AV}$ linear equation which was used to calculate apparent MW. Vc=column volume (24.0 mL), Vo=void volume (7.43 mL, determined using Blue Dextran 2000). (b) Representative gel filtration traces for the APX proteins (wtAPX, mAPX, and APEX) and representative fluorescent proteins, at a concentration of 10 µM.
Figure 8:
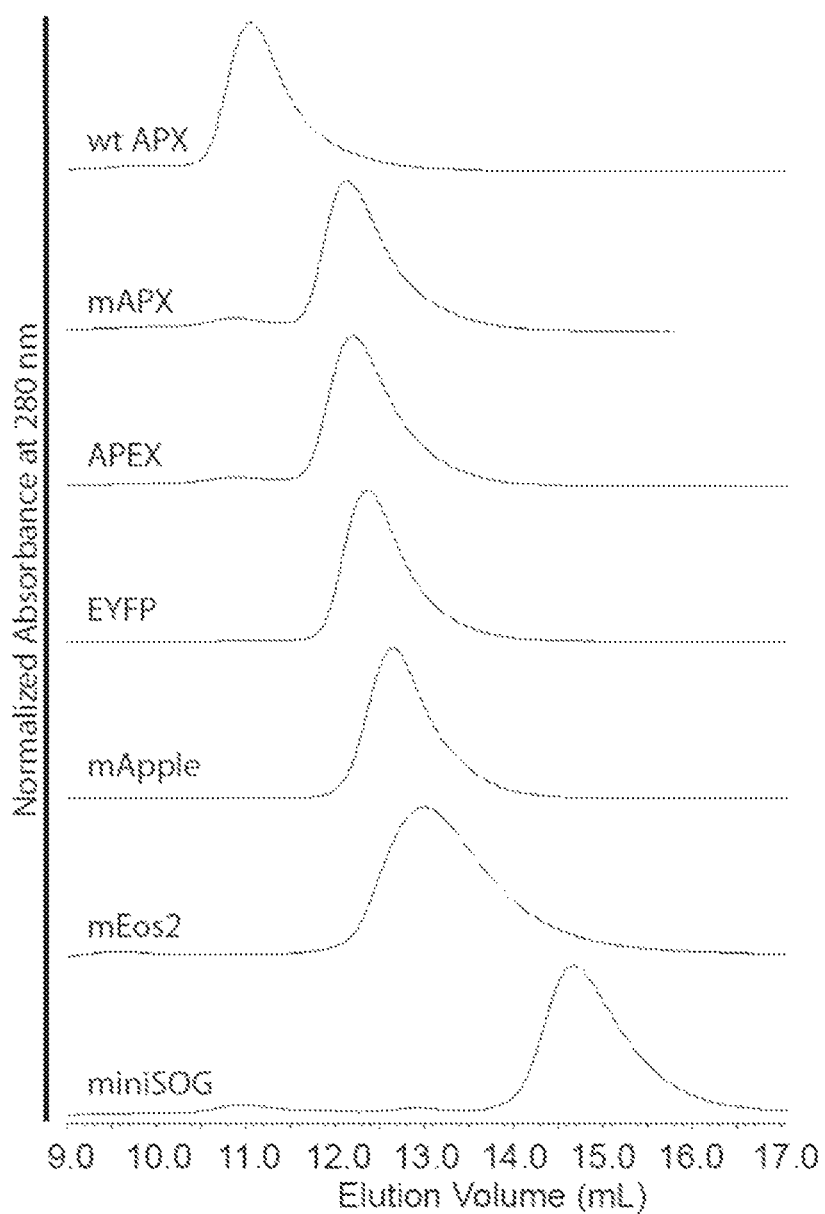

Next, monomeric APX mutants were engineered. Building upon earlier work (Mandelman, et. al., Protein Science 7, 2089-2098 (1998)), residues at the dimer interface to Lys were individually mutated to introduce negatively charged or neutral residues, to create repulsive interactions (FIG. 4b). Three mutants on the basis of sequence alignment to an isoform of maize APX that was reported to be monomeric (Koshiba, et. al., *Plant and Cell Physiology* 34, 713-721 (1993)) were also tested. Gel filtration chromatography (GFC) and SDS-PAGE was used to assess oligomerization and confirm the molecular weights of the wt APX, mutant APX, and the standards (see FIG. 8). The approximate molecular weights and the percentage of high molecular-weight aggregates of wtAPX and a number of APX mutants are shown in FIG. 4c. The calculated molecular weight (MW) of wt APX is 28 kD. As expected, wt APX runs as a dimer.

Five mutants were significantly more monomeric than wt, but they all displayed weak dimerization, so double and triple mutants were generated using permutations of the five promising single mutations. The different mutations tested consisted of at least: K31S, A233D, I185K, K14D, A28K, E112K, E228K, D229K, A28K/E112K, K14D/D229K, K14D/E228K, E112K/E228K, K14D/E112K, E112K/D229K, A28K/E112K/D229K, K14D/E112K/D229K, K14D/E112K/E228K, A28K/E112K/E228K. APX K14D/E112K exhibited the most monomericity while still expressing well in *E. coli* and forming minimal high molecular weight aggregates. For ease of reference, APX K14D/E112K is denoted mAPX. This APX mutant, having a low rate of high molecular-weight aggregate formation, was selected for further characterization.

The oligomerization of mAPX was compared to that of wt APX, miniSOG, and several fluorescent proteins (mApple, EYFP, and mEos2) across a range of concentrations. mAPX was not as monomeric as mApple, but it was comparable to EYFP and much more monomeric than both wt APX and mEos2 (McKinney, et. al., *Nat Meth* 6, 131-133 (2009)). Both mAPX and wt APX were fused to connexin43 (Cx43), a protein that is sensitive to oligomeric tags (FIG. 4d) (McKinney, et. al., *Nat Meth* 6, 131-133 (2009); Lauf, et. al., *FEBS letters* 498, 11-15 (2001)). Whereas wt APX gave rise to abnormal retention inside cells (Kumar, et. al., *Journal of Cell Science* 108, 3725-3734 (1995)), both Cx43-mAPX and Cx43-GFP-mAPX localized properly to gap junctions, indicating that despite its weak residual dimerization at high concentrations, mAPX does not disrupt Cx43 trafficking.

Next, the activity of wt APX and mAPX was compared in mammalian cells. HEK cells were transfected with the constructs indicated in FIG. 5c, incubated with (at 7 μM or 3 υM) or without exogenous heme, fixed, reacted with DAB in the presence of $H_2O_2$, then imaged and the mean fraction of transmitted light absorbed in transfected cells was determined. mAPX and wt APX were equally active in vitro (FIG. 5b) and comparably active in some cellular contexts, such as the mitochondrial matrix when assessed using DAB staining.

Figure 9:
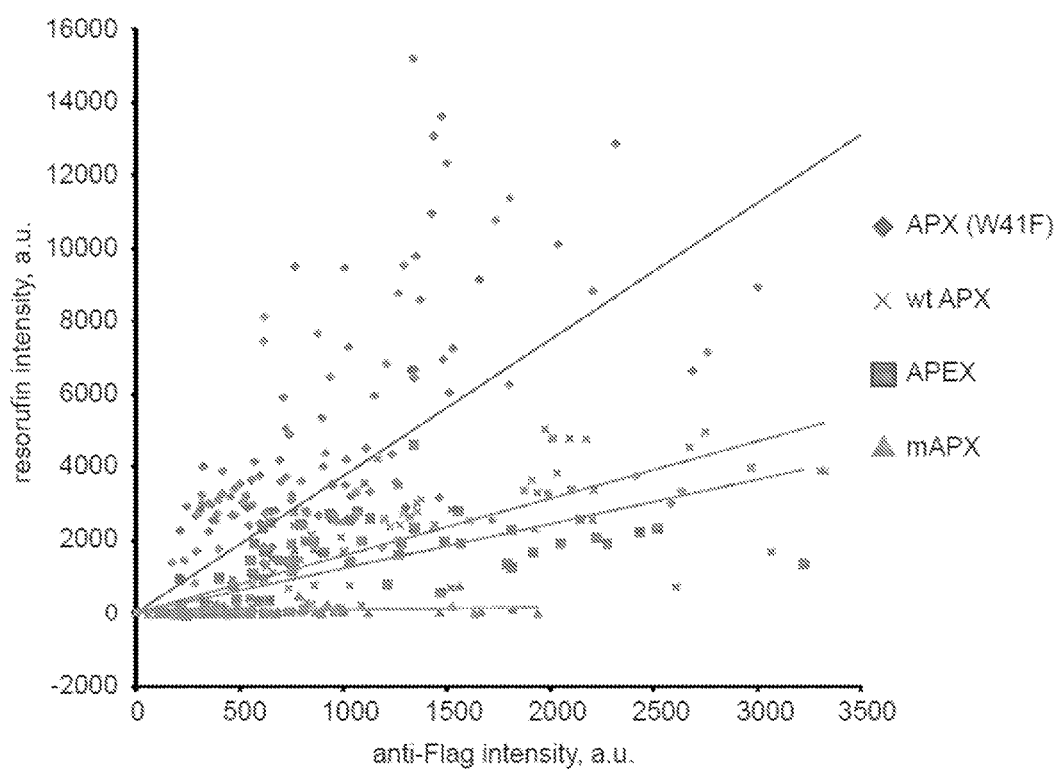
FIG. 9 is a scatter plot that shows the W41F mutation improves the activity of mAPX toward AmplexUltraRed in cells. Mean resorufin labeling intensity in a single cell is plotted against APX expression level (mean anti-flag staining intensity) in the same cell. Data are shown for >70 single cells for each APX variant.

Further, Amplex UltraRed labeling and immunostaining of wtAPX, APX$^{W41F}$, mAPX, and APEX was performed on transfected HEK293T cells. Amplex UltraRed labeling was performed for 6 minutes. All APX variants were expressed with a C-terminal nuclear export signal (NES, see Table 3). The results obtained from this study show that, when expressed throughout the cytosol via fusion to a nuclear export sequence (NES, Table 3), mAPX was less active than wt APX toward both DAB and Amplex UltraRed (FIG. 9). Culturing the cells with heme after transfection significantly boosted the activity of mAPX-NES. It was reasoned that the relatively low activity of mAPX-NES is likely due to less efficient heme incorporation in the cellular context, perhaps a result of decreased thermal stability associated with monomerization (Mandelman, et. al., *Protein Science* 7, 2089-2098 (1998)).

Altering the Substrate Binding Site of mAPX Improved Enzymatic Activity

Figure 10:
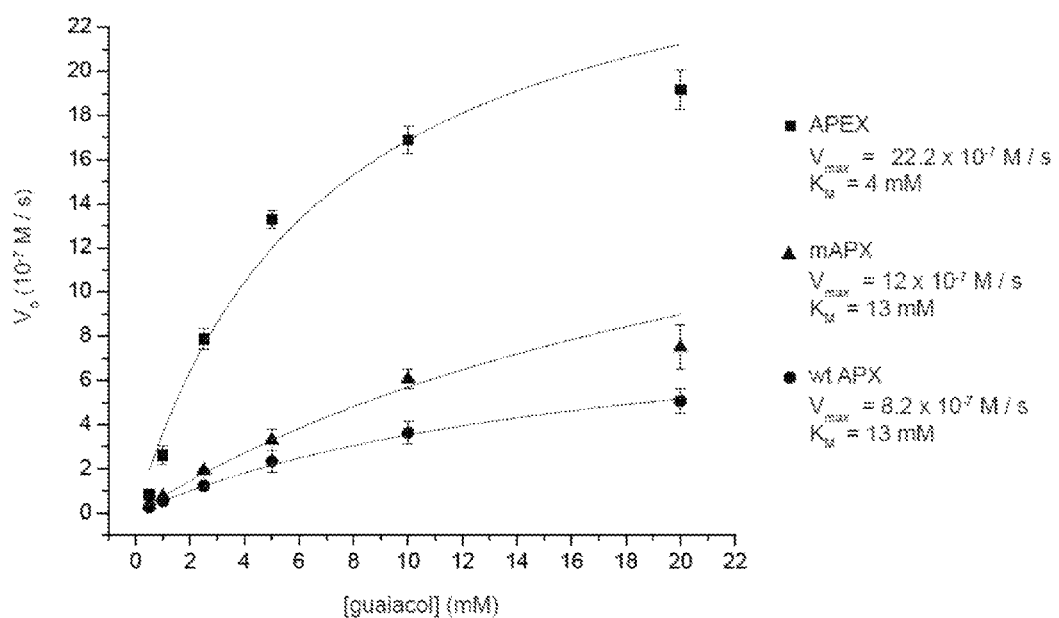
FIG. 10 shows Michaelis-Menten kinetic plots for wt APX, mAPX, and APEX with guaiacol as substrate. Data points represent the mean±standard deviation of 2-3 independent measurements. Initial rates are shown as a function of guaiacol concentration. $H_2O_2$ concentration was 90 µM, and enzyme concentration was 20 nM in all trials. Oxidation to tetraguaiacol was monitored by absorbance at 470 nm ($\epsilon_{470}=22\times10^3$ $M^{-1}$ $cm^{-1}$)$^2$.

In order to improve the performance of mAPX in mammalian cells, monomeric APX was engineered with improved activity toward DAB in the hope that faster kinetics could compensate for diminished heme binding. The substrate binding site of APX was compared to that of HRP, which has faster kinetics and broader aromatic substrate tolerance (Henriksen, et. al., *Journal of Biological Chemistry* 274, 35005-35011 (1999)). In order to make APX more HRP-like, seven mutants of APX were designed that incorporated mostly aromatic residues into the active site (FIG. 5a). A colorimetric assay was employed using guaiacol, a prototypical aromatic peroxidase substrate, to determine Michaelis-Menten parameters (Kumar, et. al., *Journal of Cell Science* 108, 3725-3734 (1995); Henriksen, et. al., *Journal of Biological Chemistry* 274, 35005-35011 (1999)) (FIG. 5b and FIG. 10). All of the mutations improved APX activity, with the most promising mutant showing >25-fold enhancement over wt APX in terms of $k_{cat}/K_M$. The most HRP-like mutant (W41F/G69F/D133A/T135F/K136F) was also the most active, validating the engineering approach.

To generate a monomeric APX with improved activity, the two mAPX mutations (K14D/E112K) were added to each of the activity-enhanced mutants. The monomerized versions of some activity-enhanced mutants performed poorly in several cellular contexts. mAPX+W41F expressed well in *E. coli*, displayed minimal high MW aggregation, and localized comparably to mAPX in cells. The sextuple mutant (K14D, E112K, W41F, D133A, T135F, K136F=mAPX–FFAF), was compared to mAPX+W41F within cells. HEK cells were transfected with constructs targeted to the mitochondrial matrix (Table 3), while COS-7 cells were transfected with constructs fused to the C-terminus of connexin 43 (Table 3). After fixation, the cells were treated with DAB and $H_2O_2$ to generate DAB polymer. Brightfield images showed the DAB stain, and fluorescence images showed the co-transfected nuclear YFP (Yellow Fluorescent Protein) marker. After fixation, cells were stained with anti-Flag (for matrix) or anti-myc (for connexin) antibody to visualize peroxidase expression levels. In the mitochondrial matrix, both mutants expressed well, but mAPX+W41F gave much stronger DAB stain. The mAPX–FFAF fusion to connexin did express, but it formed very few gap junctions and exhibited predominantly ER localization. In contrast, connexin fused to mAPX+W41F incorporated well into gap junctions and gave strong DAB stain. Therefore mAPX+W41F (K14D/E112K/W41F) was selected, denoted as "APEX" (for Enhanced APX), as the optimized reporter for subsequent experiments. Importantly, APEX–NES gave markedly stronger staining than mAPX–NES, using both DAB and Amplex UltraRed as substrates (FIG. 9). APEX is equally monomeric to mAPX in vitro (FIG. 4c) and behaves well as a fusion to Cx43, both alone and in tandem with GFP (FIG. 4d).

Example 2

Use of Ascorbate Peroxidase Mutants in Microscopy

Materials and Methods
Genetic Constructs
The genetic constructs used in this example consist of at least those found in Example 1, as exampled in Table 3.
Mammalian Cell Culture and Transfection
Culture and transfection methods were employed as described in Example 1.
Fixation and Staining with DAB, Osmium Tetroxide ($OsO_4$), and Uranyl Acetate
A solution of 4% formaldehyde (freshly depolymerized from paraformaldehyde) with 2% glutaraldehyde in 10 mM phosphate buffered saline (PBS) was added to cells 24 hours after transfection. Cells were treated for 3 min at room temperature, then 30 min on ice. Cells were then washed 5×2 min using ice cold 10 mM PBS. Cells were blocked with 20 mM glycine for 5 min on ice. Cells were then washed 5×2 min with ice-cold 10 mM PBS. Cells were then treated with an ice-cold solution of DAB (0.5 mg/mL) and $H_2O_2$ (0.03%) in 10 mM PBS for 20 min. Cells were then washed 5×2 min with ice-cold 10 mM PBS. Cells were treated with 2% $OsO_4$ in ice-cold 10 mM PBS for 30 min, then washed 5×2 min with ice-cold distilled deionized water. Cells were then placed under ice-cold 2% aqueous uranyl acetate for 24 hours.
DAB Staining and EM Preparation of Cultured Cells
Transfected cells cultured on poly-d-lysine coated glass bottom dishes (P35GC-0-14-C, MatTek Corp.) were fixed using room temperature 2% glutaraldehyde (Electron Microscopy Sciences) in 100 mM sodium cacodylate buffer with 2 mM $CaCl_2$, pH 7.4, then quickly moved to ice. Cells were kept between 0 and 4° C. for all subsequent steps until resin infiltration. After 30-60 min, cells were rinsed 5×2 min in chilled buffer, then treated for 5 min in buffer containing 20 mM glycine to quench unreacted glutaraldehyde, followed by 5×2 min rinses in chilled buffer. A freshly-diluted solution of 0.5 mg/mL 3,3′-diaminobenzidine (DAB) tetrahydrochloride or the DAB free base (Sigma) dissolved in HCl were combined with 0.03% (v/v) $H_2O_2$ in chilled buffer, and the solution was added to cells for 1 to 15 min, depending on the sample. A summary of cell types and DAB reaction times is presented in Table 3, below. The reaction product generation could be monitored by transmitted LM. To halt the reaction, the DAB solution was removed, and cells were rinsed 5×2 min with chilled buffer. For correlated LM-EM imaging of connexin43-GFP-APEX, the procedure was the same except cells were immersed in 2% glutaraldehyde for ~16 h, and regions of interest were identified by GFP fluorescence prior to treatment with DAB. After the DAB reaction was halted, cells were post-fixed for 30 min using 2% osmium tetroxide (Electron Microscopy Sciences) in chilled buffer. Cells were rinsed 5×2 min in chilled distilled water, then placed in chilled 2% aqueous uranyl acetate (Electron Microscopy Sciences) overnight. The samples were then dehydrated in a cold graded ethanol series (20%, 50%, 70%, 90%, 100%, 100%) 2 min each, rinsed once in room temperature anhydrous ethanol to avoid condensation, and infiltrated in Durcupan ACM resin (Electron Microscopy Sciences) using 1:1 anhydrous ethanol and resin for 30 min, then 100% resin 2×1 h, then into fresh resin and polymerized in a vacuum oven at 60° C. for 48 h.
DAB Photooxidation and EM Preparation of miniSOG-MCU
For photooxidation of miniSOG-MCU, cells were fixed for 30 minutes with 2% glutaraldehyde in 0.1M sodium cacodylate buffer, then rinsed in the same buffer to remove unreacted glutaraldehyde. The region of interest was identified by the fluorescence microscopy (Leica TCS SPE-II confocal imaging system) and an image recorded with care not to bleach the area. The cells were then placed in oxygenated DAB (0.5 mg/mg) in cacodylate buffer and the sample illuminated using a standard FITC filter set (EX470/40, DM510, BA520) with intense light from a 150 W xenon lamp. Illumination was stopped as soon as a very light brown reaction product began to appear in place of the green fluorescence as monitored by transmitted light (typically 3-5 minutes). The samples were then rinsed in buffer, post-fixed in 1% osmium tetroxide in cacodylate buffer for 30 minutes and dehydrated and embedded for EM using standard methods.

TABLE 4

EM staining conditions and cell types

| Construct | Cell type | Time of DAB treatment (minutes) |
|---|---|---|
| Mito matrix-APEX | COS-7 | 1 |
| APEX-ER lumen | COS-7 | 15 |
| APEX-histone2B | COS-7 | 5 |
| Vimentin-APEX | COS-7 | 5 |
| Connexin43-GFP-APEX | HEK293T | 1 |
| MCU-APEX | COS-7 | 15 |
| APEX-MCU | COS-7 | 15 |
| tdAPX$^{W41F}$-MCU | COS-7 | 5 |
| MiniSOG-MCU | Hela | 3-5 (time of photooxidation) |

Electron Microscopy
DAB-stained areas of embedded cultured cells were identified by transmitted light and the areas of interest were sawed out using a jeweler's saw and mounted on dummy acrylic blocks with cyanoacrylic adhesive. The coverslip was carefully removed, the block trimmed, and ultrathin sections were cut using an ultramicrotome. Electron micrographs recorded using a JEOL 1200 TEM operating at 80 keV.

Electron Tomography 0.5 micron thick sections of cells expressing Cx43-GFP-APEX were cut and imaged using a 4000 IVEM (JEOL) operated at 400 keV. The sections were tilted and images recorded every 2° from ±60° to −60° at 40,000 magnification. The effective pixel size was 0.37 nm. A second orthogonal tilt series was recorded as well. The image stack was aligned and reconstructions were obtained using R-weighed back projection methods with the IMOD[37] or TxBr tomography package[38].

Amplex UltraRed Staining, Immunostaining, and Fluorescence Microscopy

Transfected cells cultured on 150 μm thickness glass coverslips were moved to ice, then treated with a solution of 50 μM Amplex UltraRed (Molecular Probes) with 0.02% $H_2O_2$ in Dulbecco's phosphate-buffered saline (DPBS). The Amplex UltraRed solution was freshly diluted from a 10 mM stock in dimethyl sulfoxide (DMSO). After 5 to 30 min, depending on the sample, the Amplex UltraRed solution was removed and replaced with DPBS. In some cases, cells were imaged live. Strong resorufin signal was present in cells expressing APX, although the signal was not tightly localized to the site of origin. Alternatively, cells were fixed using freshly depolymerized 4% formaldehyde (Electron Microscopy Sciences) in PBS for 30 min on ice, rinsed 5×2 min in chilled PBS, then treated with methanol for 5-10 min at −20° C. Samples were blocked using 1% (v/v) bovine serum albumin (Fisher Scientific) in PBS at 4° C. for 30 min, then treated overnight at 4° C. with a 1:500 dilution of mouse-anti-Flag (Agilent) or chicken-anti-c-myc (Life Technologies) in PBS with 1% BSA. Cells were rinsed 4×5 min in PBS, then treated with a 1:750 dilution of AlexaFluor 488 goat anti-mouse IgG (Life Technologies) for 15 min at 4° C. Cells were rinsed 4×5 min in PBS, then imaged by confocal microscopy. At this point, much of the resorufin had been washed away, but the remaining labeling was more closely localized to the site of origin. Confocal imaging was performed with a Zeiss AxioObserver inverted microscope. Images were collected using Slidebook (Intelligent Imaging Innovations), and all image analysis was performed in SlideBook. Fluorophore channels in each experiment were normalized to the same intensity ranges. Acquisition times ranged from 100 ms to 1 s.

Gap Junction and DAB Stain Intensity Statistics in Mammalian Cells

Figure 2:
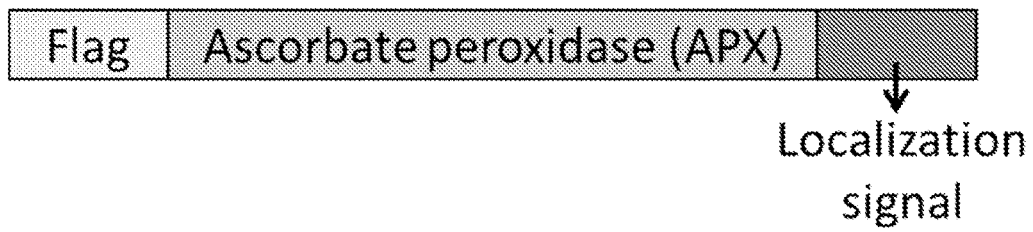
FIG. 2 is a diagram showing the structure of an exemplary APX-containing fusion proteins. Flag is an epitope tag for immunolabeling and detection. The localization signal provides for subcellular targeting of the fusion protein. See also Table 3.
Figure 3:
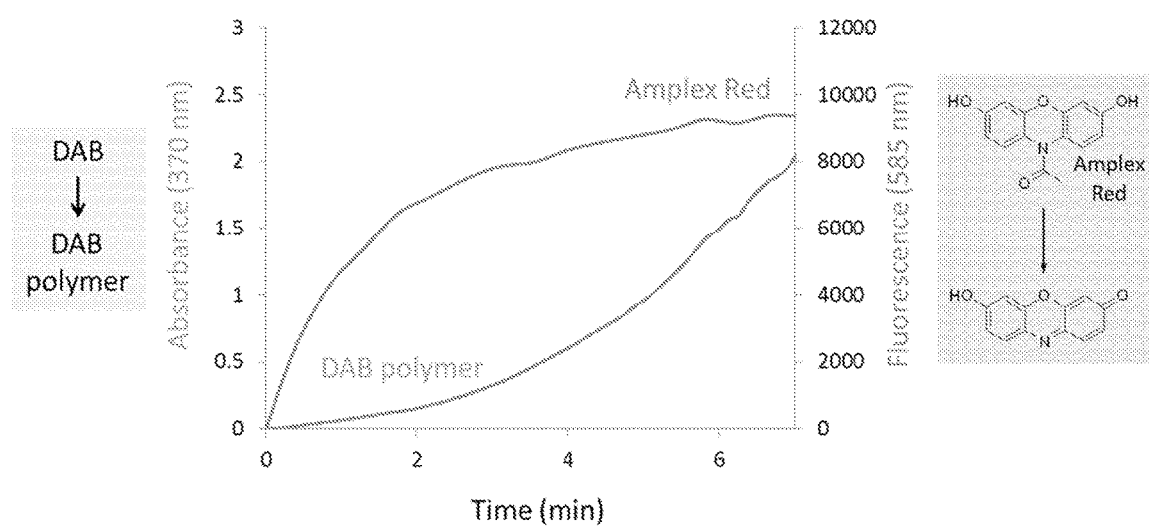
FIG. 3 is a chart showing in vitro activity of APX to convert DAB into DAB polymers and convert Amplex Red to Resorufin. Resorufin: Ex 571 nm.

Any cell displaying detectable GFP fluorescence was considered transfected. Contact sites between neighboring transfected cells were identified using DIC imaging. Gap junctions were identified as lines of GFP fluorescence unambiguously overlaying with the plasma membrane of two transfected cells based on DIC. DAB stain intensity for APX-NES variants was analyzed using SlideBook. Transfected cells were identified by nuclear YFP fluorescence. In each transfected cell, a representative DAB-stained region was encircled, and its average brightfield intensity was calculated. Background intensity, determined for each field of view by encircling a representative region in the cytosol of an untransfected cell, was subtracted out. The bar graph in FIG. 2c represents mean data from >60 transfected cells.

Results

Figure 6:
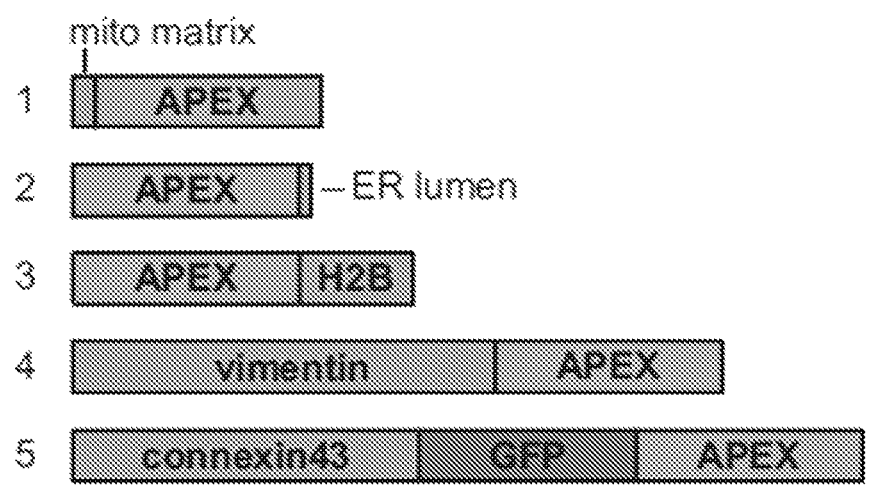
FIG. 6 shows a diagram depicting the schematics of APEX constructs used for electron microscopy of cellular proteins and organelles. (a) The constructs target APEX to the: (1) mitochondrial matrix; (2) Endoplasmic reticulum (ER) lumen; (3) chromatin; (4) vimentin intermediate filaments; (5) connexin gap junctions. See also Table 3. (b) a schematic illustration presenting the two topology models for MCU and the predicted EM staining patterns for each model when APEX is fused to either the N- or C-terminus of MCU.
Figure 6:
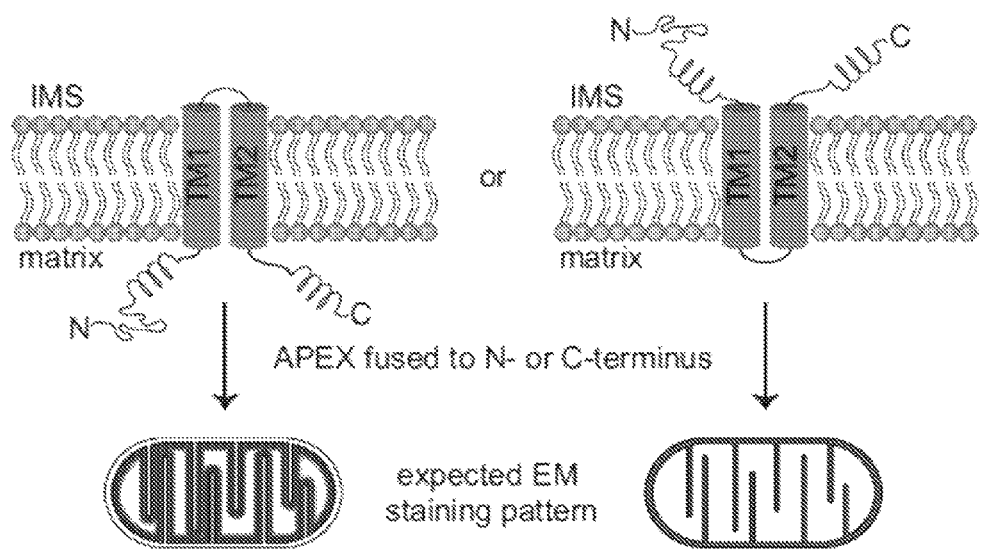

APEX Provided Excellent Resolution and High Contrast for EM Imaging in Mammalian Cells APEX ($APX^{K14D/E112K/W41F}$) was first used to stain two cellular compartments with distinct EM signatures: the mitochondrial matrix and the ER lumen. Mitochondria expressing APEX (through use of the Mito matrix-APEX construct containing the sequence MLATRVFSLVGKRA-ISTSVCVRAH (SEQ ID NO:5) which targets APEX to the mitochondria, as depicted in FIG. 6a, Table 3) showed strong contrast and well-defined cristae structures relative to non-expressing mitochondria through DAB staining of transfected COS-7 cells. When localized to the ER lumen (through use of the ER localization signal KDEL (SEQ ID NO:7), as depicted in FIG. 6a, Table 3) APEX provided dense DAB staining throughout the ER tubular network of transfected COS-7 cells. By comparison, the ER lumen of untransfected cells gave weak contrast.

EM imaging of APEX fused to three mammalian proteins: histone 2B (H2B), vimentin, and connexin43 (Cx43), was then performed. APEX-H2B fusion (depicted in FIG. 6a, Table 3) revealed detailed chromatin structures, both along the nuclear envelope and on the periphery of nucleoli. These features were not discernible in untransfected cells. APEX-H2B properly incorporated into chromatin throughout all stages of mitosis, demonstrating that the weak dimerization of APEX is non-perturbing in this context. DAB staining following expression of Vimentin-APEX (depicted in FIG. 6a, Table 3) highlighted intermediate filaments throughout the cell, and the periodicity of individual helical structures could be discerned, underscoring the excellent contrast and high resolution afforded by APEX. Cx43-GFP-APEX (depicted in FIG. 6a, Table 3) gave high-resolution images of gap junction plaques following DAB staining in transfected HEK293T cells, revealed by both thin sections and electron tomography. In some cases, gap junction plaques were closely opposed to tubular segments of ER membrane (Sosinsky, et. al., *Cell Communication and Adhesion* 10, 181-186 (2003)), but the DAB reaction product exhibited minimal spread even in the absence of membrane enclosure.

Figure 11:
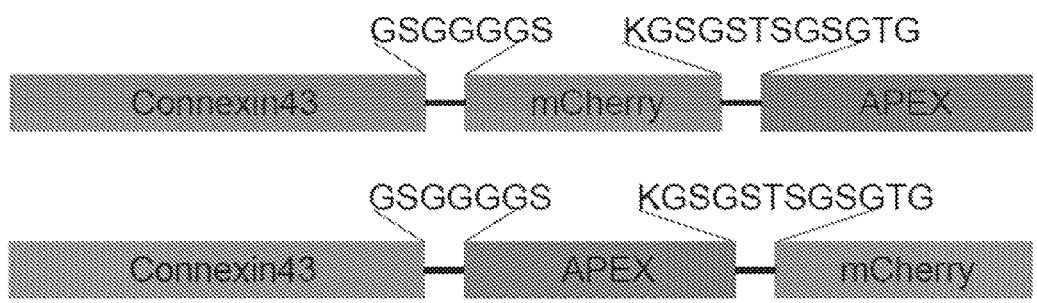
FIG. 11 shows schematics of constructs used to test the use of a red fluorescent protein (mCherry) fused to APEX and connexin 43 for gap junction labeling. GSGGGGS (SEQ ID NO:12) and KGSGSTSGSGTG (SEQ ID NO:13) are used as linkers in the construct.

Cx43-GFP-APEX was employed for correlated light microscopy (LM) and EM (Sosinsky, et. al., *Methods in Cell Biology*, Vol. Volume 79 575-591 (Academic Press, 2007)) by imaging GFP fluorescence in fixed cells, followed by DAB deposition and EM processing. Similar constructs utilizing mCherry instead of GFP (as depicted in FIG. 11, Table 3) also formed gap junctions and gave bright fluorescence and strong DAB stain, indicating that APEX can be used in tandem with both red and green fluorescent proteins for correlated LM and EM.

APEX can be Used for Membrane Protein Topology Determination by EM

Because APEX remains active after membrane-preserving fixation conditions and generates a minimally-diffusive reaction product that cannot cross membranes, it was envisioned that APEX could be useful for determination of protein topology within membranes. The topology of MCU (mitochondrial calcium uniporter), was the chosen for investigation. It has long been known that mitochondria take up calcium (DeLuca & Engstrom, *Proc. Natl. Acad. Sci. USA* 47, 1744-1750 (1961)), but the molecular identity of the channel was only recently determined to be MCU, an inner mitochondrial membrane (IM) protein with two membrane-spanning segments. Two recent reports utilized biochemical methods to map the membrane topology of MCU (Baughman, et. al., *Nature* 476, 341-345 (2011); De Stefani, et. al., *Nature* 476, 336-340 (2011)). Whereas Baughman et. al. proposed that both termini of MCU face the matrix, DeStefani et. al. reported that both termini face the intermembrane space (IMS) (FIG. 6b). To resolve this discrepancy, N- and C-terminal fusions of APEX to MCU were constructed, EM staining was performed, and the samples were imaged by EM. Consistent with the model of Baughman et. al., both constructs gave clear EM staining in the matrix, but not the IMS. Separate controls showed that APEX is highly active in the IMS.

Interestingly, the matrix stain was strongest for both constructs at sites where cristae were closely stacked (within ~25 nm). To investigate whether this localization is an artifact of APEX dimerization at high concentrations, the experiment was repeated using a tandem dimer of APX$^{W41F}$ (two APX$^{W41F}$ proteins linked with a short amino acid chain, denoted tdAPX) as well as miniSOG in place of APEX. Additionally, gel filtration chromatography (GFC) was used to assess the relative abundance of oligomers that formed at increasing tdAPX concentrations in vitro (5 µM, 20 µM, and 47 µM). Three different linker lengths (18, 23, and 28 amino acids) were tested. His6-tagged proteins were expressed and purified from E. coli. All three variants gave a major peak with an apparent molecular weight (MW) of ~56 kDa, as expected for tdAPX. The apparent MW of the major peak remained constant as a function of concentration for all three constructs. In addition to the major peak, each tdAPX variant exhibited a high MW aggregate peak (eluted with void volume) and a peak with an apparent MW of ~105 kDa, which roughly corresponds to a tetramer. The fact that a distinct peak was observed suggests that an oligomer was formed irreversibly on the time scale of the chromatography (35 min). This ~105 kDa oligomer was highly abundant for the 18 amino acid linker variant, but minimal for the variant with a 28 amino acid linker. Therefore, the 28 amino acid linker variant was selected as the optimized tandem dimer to be used in EM experiments. Identical EM staining patterns were obtained for all constructs (MCU-APEX, APEX-MCU, tdAPX$^{W41F}$, Table 3), although artifactual dimerization (because miniSOG, like APEX, shows weak oligomerization at concentrations above ~20 uM) cannot be completely ruled out (FIG. 4d).

In a functional assay for $Ca^{2+}$ uptake, all fusions of MCU to APEX, tdAPX$^{W41F}$, and miniSOG performed comparably to MCU appended to a small Flag epitope tag (data not shown), indicating that none of these tags perturb function. The MCU topology revealed by APEX EM imaging has implications for MCU interaction partners and signaling effectors, as it is now clear that most of the soluble portions of the protein reside in the matrix, rather than the IMS.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An imaging method, comprising:
   providing a sample containing a cell that expresses a Class I heme peroxidase, or a fusion protein comprising (a) the Class I heme peroxidase, and (b) a protein or a cellular localization signal peptide, and
   contacting the sample with a substrate of the Class I heme peroxidase to allow conversion of the substrate into a product via an oxidation reaction catalyzed by the Class I heme peroxidase, wherein the product releases a signal detectable by a microscope.

2. The method of claim 1, further comprising detecting the signal under a microscope.

3. The method of claim 1 wherein the substrate is 3-methyl-2-benzothiazolinone hydrazone, 2,2'-azino-bis(3-ethylbenzthiazoline-6-sulfonic acid), a phenol, or an aniline.

4. The method of claim 3, wherein the phenol is selected from the group consisting of guaiacol, pyrogallol, Amplex UltraRed, dihydrofluorescin, p-cresol, dopamine, 3-methylphenol, 4-methoxyphenol, 4-hydroxybenzaldehyde, 5-aminosalicylic acid, and 4-chloro-1-naphthol.

5. The method of claim 3, wherein the aniline is selected from the group consisting of diaminobenzidine (DAB), 3-amino-9-ethylcarbazole, o-phenylenediamine, 3,3',5,5'-tetramethylbenzidine, o-dianisidine, 5-aminosalicylic acid, Luminol, 4-aminophthalhydrazide, N-(6-Aminohexyl)-N-ethylisoluminol, N-(4-Aminobutyl)-N-ethylisoluminol, 3-methylaniline, 4-methylaniline, and 4-methoxyaniline.

6. The method of claim 1 wherein the Class I heme peroxidase is an ascorbate peroxidase (APX), a yeast cytochrome c peroxidase (CCP), or a bacterial catalase-peroxidase (BCP).

7. The method of claim 1 wherein the Class I heme peroxidase is monomeric.

8. The method of claim 7, wherein the Class I heme peroxidase is a mutated APX, which, as compared to its wild-type counterpart, contains
   (i) one or more mutations at positions corresponding to K14, E17, K18, K20, R21, R24, A28, E106, E112, I185, E228, and D229 in SEQ ID NO:1; or
   (ii) one or more mutations at positions corresponding to W41, G69, D133, T135, and K136 in SEQ ID NO:1.

9. The method of claim 8, wherein the mutant APX is:
   (a) single mutant K14D, single mutant A28K, single mutant E112K, single mutant E228K, single mutant D229K, double mutant K14D/E112K, double mutant K14D/E228K, double mutant K14D/D229K, double mutant A28K/E112K, double mutant E112K/E228K, double mutant E112K/D229K, triple mutant E17N/K20A/R21L, triple mutant A28K/E112K/D229K, triple mutant K14D/E112K/D229K, triple mutant K14D/E112K/E228K, triple mutant A28K/E112K/E228K, or triple mutant K14D/W41F/E112K,
   (b) single mutant W41F, single mutant G69F, single mutant G174F, double mutant W41F/G69F, triple mutant D133A/T135F/K136F, quadruple mutant W41F/D133A/T135F/K136F, quadruple mutant G69F/D133A/T135F/K136F, or quintuple mutant W41F/G69F/D133A/T135F/K136F, or
   (c) a combination of (a) and (b).

10. The method of claim 6, wherein the Class I heme peroxidase is a mutated yeast CCP, which, as compared to its wild-type counterpart, comprises one or more amino acid substitutions at positions corresponding to W51, S81, D146, D148, K149, and G186 in SEQ ID NO:2.

11. The method of claim 6, wherein the Class I heme peroxidase is a mutated BCP, which, as compared to its wild-type counterpart, comprises one or more amino acid residue substitutions at positions corresponding to W107, D137, N231, E223, and G316 in SEQ ID NO:3.

12. The method of claim 1 wherein the fusion protein comprises the Class I heme peroxidase and the protein.

13. The method of claim 1, wherein the cellular localization signal peptide is an ER-targeting signal peptide, a Golgi-targeting signal peptide, a mitochondria-targeting signal peptide, a nuclear localization signal peptide, or a nuclear export signal peptide.

14. The method of claim 13, wherein the cellular localization signal peptide comprises an amino acid sequence selected from the group consisting of:

| | |
|---|---|
| DPVVVLGLCLSCLLLLSLWKQSYGGG, | (SEQ ID NO: 4) |
| MLATRVFSLVGKRAISTSVCVRAH, | (SEQ ID NO: 5) |
| LQLPPLERLTLD, and | (SEQ ID NO: 6) |
| KDEL. | (SEQ ID NO: 7) |

15. The method of claim 1 wherein the Class I heme peroxidase or the fusion protein comprises a protein tag.

16. The method of claim 1 wherein the cell that expresses the Class I heme peroxidase or the fusion protein is a mammalian cell, a bacterial cell, or a yeast cell.

17. The method of claim 1 wherein the sample is a tissue sample.

18. The method of claim 2 wherein in the detecting step, the sample contains either a live cell or a fixed cell.

* * * * *

UNITED STATES PATENT AND TRADEMARK OFFICE
CERTIFICATE OF CORRECTION

PATENT NO. : 9,663,815 B2  Page 1 of 1
APPLICATION NO. : 14/345309
DATED : May 30, 2017
INVENTOR(S) : Alice Y. Ting et al.

It is certified that error appears in the above-identified patent and that said Letters Patent is hereby corrected as shown below:

At Column 45, Claim 8, Line 40 delete "1185" and replace with "I185".

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*